(12) United States Patent
Dedhar

(10) Patent No.: US 6,518,397 B1
(45) Date of Patent: *Feb. 11, 2003

(54) PHARMACEUTICALS FOR MODULATING HORMONE RESPONSIVENESS

(76) Inventor: Shoukat Dedhar, #1-219 East 8th St., North Vancouver B.C. (CA), V7L 1Y9

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/900,241

(22) Filed: Jul. 24, 1997

Related U.S. Application Data

(63) Continuation-in-part of application No. 08/377,432, filed as application No. PCT/CA95/00664 on Nov. 23, 1995, now Pat. No. 5,854,202.

(51) Int. Cl.$^7$ .............................. C07K 1/00; A61K 38/18
(52) U.S. Cl. ....................... 530/300; 530/329; 530/328; 530/327; 530/326; 530/325; 530/324; 514/2; 514/12; 514/13; 514/14; 514/15; 514/16; 514/17
(58) Field of Search .................................. 530/300, 329, 530/328, 327, 326, 325, 324; 514/2, 12, 13, 14, 15, 16, 17

(56) References Cited

U.S. PATENT DOCUMENTS

| | | | |
|---|---|---|---|
| 4,895,719 | A | 1/1990 | Radhakrishnan et al. |
| 5,217,867 | A | 6/1993 | Evans et al. |
| 5,298,429 | A | 3/1994 | Evans et al. |
| 5,389,517 | A | 2/1995 | Wotiz et al. |
| 5,426,097 | A | 6/1995 | Stern et al. |

FOREIGN PATENT DOCUMENTS

| | | |
|---|---|---|
| CA | 2140814 A | 8/1996 |
| WO | WO93/14098 | 7/1993 |
| WO | WO96/23001 | 8/1996 |

OTHER PUBLICATIONS

Stryer, Biochemistry, W.H. Freeman and Company, San Francisco, pp. 13–16, 1981.*
Morgan et al. Ann. Rep. Med. Chem. 24(243–252) 1989.*
Dedhar et al., "Inhibition of Nuclear Hormone Receptor Activity by Calreticulin", Nature, vol. 367, pp. 480–483 (Feb. 3, 1994).
Rojiani et al., "In Vitro Interaction of a Polypeptide Homologous to Human Ro/SS–A Antigen (Calreticulin) with a Highly Conserved Amino Acid Sequence in the Cytoplasmic Domain of Integrin α Subunits", Biochemistry, vol. 30, No. 41, pp. 9859–9866 (1991).

Burns et al., "Modulation of Gene Expression by Calreticulin Binding to the Glucocorticoid Receptor", Nature, vol. 367, pp. 476–480 (Feb. 3, 1994).
Shoukat Dedhar, "Novel Functions for Calreticulin: Interaction with Integrins and Modulation of Gene Expression", Trends in Biochemical Sciences, vol. 19, No. 7, pp. 269–271 (Jul. 1994).
Michalak et al., "Calreticulin", Biochemistry Journal, vol. 285, pp. 681–692 (1992).
Dedhar et al., "Specific Alterations in the Expression of α3β1 and α6β4 Integrins in Highly Invasive and Metastatic Variants of Human Prostate Carcinoma Cells Selected by in vitro Invasion Through Reconstituted Basement Membrane", Clinical & Experimental Metastasis, vol. 11, No. 5, pp. 391–400 (1993).
Leung–Hagesteijn et al., "Cell Attachment to Extracellular Matrix Substrates is Inhibited Upon Downregulation of Expression of Calreticulin, an Intracellular Integrin α–subunit–binding Protein", Journal of Cell Science, vol. 107, pp. 589–600 (1994).
Tini et al., "An Everted Repeat Mediates Retinoic Acid Induction of the γF–Crystallin Gene: Evidence of a Direct Role for Retinoids in Lens Development", Genes & Development, vol. 7, pp. 295–307, (1993).
Pratt et al., "Estrogen and Antiestrogen Modulation of MCF7 Human Breast Cancer Cell Proliferation is Associated with Specific Alterations in Accumulation of Insulin–like Growth Factor–binding Proteins in Conditioned Media", Cancer Research, vol. 53, pp. 5193–5198 (Nov. 1, 1993).
Morrison et al., "Prediction of Bone Density from Vitamin D Receptor Alleles", Nature, vol. 367, pp. 284–287 (Jan. 20, 1994).

(List continued on next page.)

Primary Examiner—Yvonne Eyler
Assistant Examiner—Michael T. Brannock
(74) Attorney, Agent, or Firm—Burns, Doane, Swecker & Mathis, L.L.P.

(57) ABSTRACT

This invention relates to isolated and purified proteins, such as calreticulin and mimetics and inhibitors of calreticulin, for a novel use of modulating hormone responsiveness. These proteins are useful in gene therapy and in manufacturing pharmaceuticals for treating a variety of diseases, including cancer, osteoporosis and chronic inflammatory disease. The proteins include or bind to an amino acid sequence [SEQ ID NO: 1] KXFFX$^1$R, wherein X is either G, A or V and Y is either K or R. This sequence is present in the DNA-binding domain, and is critical for the DNA binding activity, of a variety of hormone receptors, including glucocorticoid receptor, minerolcorticoid receptor, androgen receptor, progesterone receptor, estrogen receptor, retinoic acid receptor, thyroid hormone receptor and vitamin D receptor. Proteins which bind to this sequence may inhibit hormone receptor induced gene transcription. Proteins which include this sequence may promote hormone receptor induced gene transcription.

4 Claims, 11 Drawing Sheets

OTHER PUBLICATIONS

Giguère et al., "Molecular Cloning of cDNA Encoding a Second Cellular Retinoic Acid–binding Protein", *Proc. Natl. Acad. Sci. USA,* vol. 87, pp. 6233–6237 (Aug. 1990).

Luisi et al., "Crystallographic Analysis of the Interaction of the Glucocorticoid Receptor with DNA", *Nature,* vol. 352, pp. 497–505 (Aug. 8, 1991).

Härd et al., "Solution Structure of the Glucocorticoid Receptor DNA–Binding Domain", *Science,* vol. 249, pp. 157–160 (Jul. 13, 1990).

Sucov et al., "Characterization of an Autoregulated Response Element in the Mouse Retinoic Acid Receptor Type β Gene", *Proc. Natl. Acad. Sci. USA,* vol. 87, pp. 5392–5396 (Jul. 1990).

Tilley et al., "Androgen Receptor Gene Expression in Human Prostate Carcinoma Cell Lines", *Cancer Research,* vol. 50, pp. 5382–5386 (Sep. 1, 1990).

Quarmby et al., "Expression and Localization of Androgen Receptor in the R–3327 Dunning Rat Prostatic Adenocarcinoma", *Cancer Research,* vol. 50, pp. 735–739 (Feb. 1, 1990).

Baksh and Michalak, "Expression of Calreticulin in *Escherichia coli* and Identification of Its $Ca^{2+}$ Binding Domains", *The Journal of Biological Chemistry,* vol. 266, No. 32, pp. 21458–21465 (Nov. 15, 1991).

Fliegel et al., "Molecular Cloning of the High Affinity Calcium–binding Protein (Calreticulin) of Skeletal Muscle Sarcoplasmic Reticulum", *The Journal of Biological Chemistry,* vol. 264, No. 36, pp. 21522–21528 (Dec. 25, 1989).

Donald S. Coffey, "Prostate Cancer an Overview of an Increasing Dilemma", *Cancer Supplement,* vol. 71, No. 3, pp. 880–886 (Feb. 1, 1993).

Peter J. Fuller, "The Steroid Receptor Superfamily: Mechanisms of Diversity", *the FASEB Journal,* vol. 5, pp. 3092–3099 (Dec. 1991).

Lebeau et al., "P59, an hsp 90–binding Protein", *The Journal of Biological Chemistry,* vol. 267, No. 7, pp. 4281–4284 (Mar. 5, 1992).

Scardino et al., "Early Detection of Prostate Cancer", *Human Pathology,* vol. 23, No. 3, pp. 211–222 (Mar. 1992).

Tilley et al., "Detection of Discrete Androgen Receptor Epitopes in Prostate Cancer by Immunostaining: Measurement by Color Video Image Analysis", *Cancer Research,* vol. 54, pp. 4096–4102 (Aug. 1, 1994).

Alexander et al., "Characterization of Posttranslational Modifications in Neuron–specific Class III β–tubulin by Mass Spectometry", *Proc. Natl. Acad. Sci. USA,* vol. 88, pp. 4685–4689 (Jun. 1991).

McCauliffe et al., "Molecular Cloning, Expression, and Chromosome 19 Localization of a Human Ro/SS–A Autoantigen", *J. Clin. Invest.,* vol. 85, pp. 1379–1391 (May 1990).

McBurney and Rogers, "Brief Notes Isolation of Male Embryonal Carcinoma Cells and Their Chromosome Replication Patterns", *Developmental Biology,* vol. 89, pp. 503–508 (1982).

Seed and Sheen, "A Simple Phase–extraction Assay for Chloramphenicol Acyltransferase Activity", *Gene,* vol. 67, pp. 271–277 (1988).

Boring et al., "Cancer Statistics, 1993", *CA Cancer J Clin,* vol. 43, No. 1, pp. 7–26 (Jan./Feb. 1993).

Darcy et al., "Mammary Organoids from Immature Virgin Rats Undergo Ductal and Alveolar Morphogenesis when Grown within a Reconstituted Basement Membrane", *Experimental Cell Research,* vol. 196, pp. 49–65 (1991).

Hsu et al., "Use of Avidin–Biotin–Peroxidase Complex (ABC) in Immunoperoxidase Techniques", *The Journal of Histochemistry and Cytochemistry,* vol. 29, No. 4, pp. 577–580 (1981).

Kozlowski et al., "Advanced Prostatic Carcinoma", *Urologic Clinics of North America,* vol. 18, No. 1, pp. 15–24, (Feb. 1991).

Lee et al., "The Expression and Posstranslational Modification of a Neuron–Specific β–Tubulin Isotype During Chick Embryogenesis", *Cell Motility and the Cytoskeleton,* vol. 17, pp. 118–132 (1990).

Bert O'Malley, "The Steroid Receptor Superfamily: More Excitement Predicted for the Future", *Molecular Endocrinology,* vol. 4, No. 3, pp. 363–369 (1990).

Opas et al., "Regulation of Expression and Intracellular Distribution of Calreticulin, a Major Calcium Binding Protein of Nonmuscle Cells", *Journal of Cellular Physiology,* vol. 149, pp. 160–171 (1991).

Cao et al., "Cloning of the Promoter for the Avian Integrin $β_3$ Subunit Gene and Its Regulation by 1,25–Dihydroxyvitamin $D_3$", *The Journal of Biological Chemistry,* vol. 268, No. 36, Issue of December 25, pp. 27371–27380 (1993).

Tai et al., "Association of a 59–Kilodalton Immunophilin with the Glucocorticoid Receptor Complex", *Science,* vol. 256, pp. 1315–1318 (May. 29, 1992).

McCauliffe et al., "A Human Ro/SS–A Autoantigen is the Homologue of Calreticulin and is Highly Homologous with Onchocercal RAL–1 Antigen and an Aplysia 'Memory Molecule'", *J. Clin. Invest.,* vol. 86, pp. 332–335 (Jul. 1990).

Darbre and King, "Progression to Steroid Insensitivity Can Occur Irrespective of the Presence of Functional Steroid Receptors", *Cell,* vol. 51, pp. 521–528 (Nov. 20, 1987).

Richard J. Stanten, "Clinical Review 37", *Journal of Clinical Endocrinology and Metabolism,* vol. 75, No. 3, pp. 685–689 (1992).

Murthy et al., "Structural homology between the rat calreticulin gene product and the *Onchocerca volvulus* antigen Ral–1" *Nucleic Acids Research* 18(16) 4933.

Burns et al., *Mol. Biol. Cell,* 4 Supp.: 135A (1993).

Desai et al., *J. Biol. Chem.,* 271:15153–15159 (1991).

Bowie et al., *Science,* 247: 1306–1310 (1990).

Ngo et al., "The Protein Folding Problem and Tertiary Structure Prediction", Merz et al., Editors, Birkauser, boston (1994).

Coppolino et al., "Calreticulin is essential for integrin–mediated calcium signalling and cell adhesion", *Nature,* vol. 386, Apr. 24, 1997, pp. 843–847.

Y. Choi, et al., "Tissue–specific and developmental regulation of a gene encoding a low–molecular weight sulfur–rich protein in soybean seeds", *Mo. Gen. Genet.,* vol. 246, (1995), pp. 266–268.

\* cited by examiner

| AR | + | + | + | + | + | + | + | + | + | + | + | + |
|---|---|---|---|---|---|---|---|---|---|---|---|---|
| CRJ | - | - | - | - | + | + | + | + | + | + | + | + |
| Peptide | - | - | - | KVFFKR | 285 | 409 | 410 | 411 | 412 | 413 | 414 | 415 | 416 | 417 |
| SEQ ID No: | | | | 3 | 3 | 5 | 2 | 4 | 50 | 51 | 52 | 53 | 54 | 55 |

| | KVFFKR | + |
|---|---|---|
| | 285 | + |
| | 409 | + |
| | 410 | + |
| | 411 | + |
| | 412 | ++ |
| | 413 | - |
| | 414 | ++ |
| | 415 | + |
| | 416 | - |
| | 417 | - |

FIG. 5B

PHARMACEUTICALS FOR MODULATING HORMONE RESPONSIVENESS

CROSS-REFERENCE TO RELATED APPLICATIONS

This application is a continuation-in-part of U.S. application Ser. No. 08/377,432 now U.S. Pat. No. 5,854,202 filed Jan. 24, 1995, entitled Novel Use of Calreticulin in Modulating Hormone Responsiveness and New Pharmaceuticals for Treating Cancer, Osteoporosis and Chronic Inflammatory Disease which is incorporated herein by reference in its entirety. This application claims priority to International Patent Application Serial No. PCT/CA95/00664 filed Nov. 23, 1995 which is also incorporated herein by reference in its entirety.

BACKGROUND OF THE INVENTION

The physiology of many organs in mammals is regulated by hormones. These hormones include steroid hormones, thyroid hormones, metabolites of vitamins, such as all trans retinoic acid, 9-cis retinoic acid, vitamin D and its metabolite 1,25 dihydroxyvitamin D3. These hormones bind to intracellular receptors which regulate expression of genes (O'Malley, 1990).

There are a variety of receptors which respond to hormones. Osteoblasts and osteoclasts respond to steroid hormones, vitamin D and retinoic acid. Mammary epithelial cells and breast carcinoma cells respond to estrogens, progesterone, retinoic acid and glucocorticoids. Lymphocytes respond to glucocorticoids.

The response of receptors to hormones is particularly important in the development of a number of diseases, including cancer, osteoporosis and chronic inflammatory disease. For example, the vitamin D receptor is strongly implicated in the evolution of osteoporosis (Morrison, 1994).

The hormone receptor family is called the nuclear hormone receptor family and consists not only of receptors whose ligands are known, but also of an increasing number of orphan receptors whose ligands are unknown (O'Malley, 1990).

The nuclear hormone receptors can be divided into several domains which include the hormone (ligand) binding domain, the DNA-binding domain and the transactivation domain (O'Malley, 1990). The DNA-binding domain consists of two zinc fingers and is responsible for the receptor's binding to the DNA response elements which are found in the promoter and enhancer regions of the genes whose expression are regulated by these receptors. Once a hormone binds to its receptor, the receptor binds to the DNA thereby inducing gene transcription.

Proteins which modulate hormone receptor induced gene transcription are poorly understood. Such proteins are present in the nucleus of the cell and inhibit or promote the binding of a hormone to its receptor.

To help design pharmaceuticals and therapies for certain diseases, one must understand the function of certain intracellular proteins and their role in modulating hormone responsiveness. Isolation and purification of these proteins would help in assessing whether they inhibit or promote hormone receptor induced gene transcription. Once such proteins are isolated, manipulation of such proteins could further inhibit or promote hormone receptor induced gene transcription. Synthetic peptides which bind to such proteins could be used to promote hormone receptor induced gene transcription. Pharmaceuticals including such peptides or their mimetics could be used to inhibit hormone receptor induced gene transcription. Gene therapy could be used to inhibit or promote hormone receptor induced gene transcription.

A need exists to identify amino acid sequences that are conserved in hormone receptors, so that particular peptides and proteins may be designed and used in modulating hormone responsiveness. This would lead to improved methods of treating a variety of diseases, disorders and abnormal physical states in mammals by regulating hormone receptor induced gene transcription in mammalian cells.

Calreticulin was initially identified as the major $Ca^{2+}$-storage protein in the sarcoplasmic reticulum of skeletal muscle (Ostwald and MacLennan, 1974). Subsequent work has revealed that the protein can also be detected in the endoplasmic reticulum of non-muscle tissues (Fliegel et al., 1989a; Opas et al., 1991). Calreticulin has been considered to be a resident protein of the endoplasmic reticulum of a cell, where it is thought to behave as a calcium binding protein due to its high capacity calcium binding properties (Michalak et al., 1992). Calreticulin possesses many diverse functional domains such as high affinity, low capacity- and low affinity, high capacity-$Ca^{2+}$-binding sites, a C-terminal KDEL endoplasmic reticulum retention signal, and a nuclear localization signal (Michalak et al., 1992).

It has been suspected that calreticulin is also present in the nucleus of a cell (Opas et al., 1991), and it has been shown to have a consensus nuclear localization sequence (Michalak, 1992) which is highly homologous to that of histone proteins. However, before this invention, its presence in the nucleus was unconfirmed and its function in the nucleus was unknown.

SUMMARY OF THE INVENTION

This invention relates to isolated and purified proteins, such as calreticulin and mimetics of calreticulin, for a novel use of modulating hormone responsiveness. These proteins are useful in gene therapy and in manufacturing pharmaceuticals for treating a variety of diseases, including cancer, osteoporosis and chronic inflammatory disease. The proteins bind to an amino acid sequence $KXFFX^1R$, wherein X is either G, A or V and $X^1$ is either K or R [SEQ ID NO:1]. This sequence is present in the DNA-binding domain, and is critical for the DNA binding activity of a variety of hormone receptors, including glucocorticoid receptor, mineralcorticoid receptor, androgen receptor, progesterone receptor, estrogen receptor, retinoic acid receptor, thyroid hormone receptor and vitamin D receptor. Proteins which bind to this sequence inhibit hormone receptor induced gene transcription. The invention includes isolated DNA molecules for these proteins, methods of treating diseases using these proteins, synthetic peptides and their mimetics, and kits containing these proteins, synthetic peptides or their mimetics.

This invention relates to a peptide and peptide mimetic having the amino acid sequence [SEQ ID NO:1] $KXFFX^1R$, wherein X is either G, A or V and $X^1$ is either K or R which promotes hormone receptor induced gene transcription. The invention includes isolated DNA molecules for these peptides, methods of treating diseases using these peptides, synthetic peptides and their mimetics, and kits containing these proteins, synthetic peptides or their mimetics. Preferably the peptides or peptide mimetics are from 6 to 100 amino acids.

This invention relates to a product for modulating hormone responsiveness. Preferably such a product is calreticulin which inhibits hormone receptor induced gene transcription. More preferably, the product is the N-domain of calreticulin. In another case, the product is a mimetic of calreticulin. The product binds to the amino acid sequence [SEQ ID NO:1] KXFFX$^1$R, wherein X is G, A or V and wherein X$^1$ is K or R.

In another case, the product for modulating hormone responsiveness is an antibody to calreticulin or a short peptide which binds to calreticulin. Such an antibody or peptide could promote hormone induced gene transcription by inhibiting calreticulin-hormone receptor interactions.

This invention relates to a peptide or peptide mimetic selected from a group [SEQ ID NOS:2–6] consisting of: KGFFRR, KVFFKR, KAFFKR, KGFFKR, TGFFKR or modified derivatives of these peptides. Preferably the peptide is from 6 to 100 amino acids.

This invention also relates to a peptide or peptide mimetic which reverses selectively calreticulin inhibitions of receptor binding to DNA response elements is part of this invention. One peptide which reverses selectively calreticulin inhibitions of retinoic acid to its DNA response elements is KLDFFKR [SEQ ID NO:45]. Another peptide which reverses selectively calreticulin inhibitions of androgen receptor binding to its DNA response elements is a peptide comprising a sequence selected from a group consisting of GLGFFKR [SEQ ID NO: 44], KLGFFGR [SEQ ID NO:48] and KLGFFKG [SEQ ID NO:49]. Preferably these peptides are from 6 to 100 amino acids.

The invention described in this patent application includes an isolated DNA molecule encoding an amino acid sequence for use in modulating hormone responsiveness. The isolated DNA molecule may encode the amino acid sequence for calreticulin. It may encode the amino acid sequence for part of a mimetic of calreticulin. It may encode a first amino acid sequence that binds to a second amino acid sequence [SEQ ID NO:1] KXFFX$^1$R, wherein X is G, A or V and wherein X$^1$ is K or R.

The invention described in this patent application includes a method of treating a disease, disorder or abnormal physical state in a mammal by regulating hormone receptor induced gene transcription in a cell. The method could include regulating the activity, quantity or stability of a peptide or peptide mimetic of the present invention for use in hormone receptor induced gene transcription. The peptide could be one that includes or binds to the amino acid sequence [SEQ ID NO:1] KXFFX$^1$R, wherein X is G, A or V and wherein X$^1$ is K or R. One protein which binds to such sequence is calreticulin. The hormone receptor could be one selected from a group consisting of: glucocorticoid receptor, mineral corticoid receptor, androgen receptor, progesterone receptor, estrogen receptor, retinoic acid receptor, thyroid hormone receptor, vitamin D receptor and orphan receptors. The disease or disorder could be one selected from a group consisting of breast cancer, prostate cancer, promyelocytic leukemia, solid tumors, chronic inflammatory disease, such as arthritis and osteoporosis.

The method of treating the disease could include administering to the mammal a pharmaceutical comprising a peptide, or a peptide mimetic of the invention and a pharmaceutical carrier. Another method of treating the disease could include administering to the mammal a pharmaceutical comprising an inhibitor of the protein and a carrier. A suitable carrier could be a lipid vesicle. As an alternative, the method could include decreasing or eliminating the quantity of calreticulin present in the cell; or decreasing the stability of calreticulin present in a cell.

In another embodiment, the invention is an isolated and purified peptide with the amino acid sequence KGX$_1$X$_2$X$_3$R where one or more of X$_1$, X$_2$ or X$_3$ is a basic amino acid [SEQ ID NO:67], and the peptide binds to calreticulin. In a preferred embodiment X$_1$, X$_2$ or X$_3$ are selected from the group consisting of lysine, arginine, histidine, phenylalanine and tyrosine. More preferably, at least one of X$^1$, X$_2$ or X$_3$ is arginine. The peptide can be one of the group consisting of KGRFKR [SEQ ID NO:52], KGFRKR [SEQ ID NO:53], KGRFRR [SEQ ID NO:58] and KGFRRR [SEQ ID NO:59]. Preferably, the peptide is from about 6 to 100 amino acids. The invention also includes a pharmaceutical composition comprising the peptide and a pharmaceutically acceptable carrier. In a preferred embodiment, the carrier is a lipid vesicle.

In another embodiment, the invention is an isolated and purified peptide comprising an amino acid sequence selected from the group consisting of KV$_{(N-acetylated)}$AFKR [SEQ ID NO:63], KVFFKR [SEQ ID NO:3], KGFFKR [SEQ ID NO:5], KAFFKR [SEQ ID NO:4], GGFFRR [SEQ ID NO:56], KVFFKR (all D-amino acids), KGFFKR (all D-amino acids), KGFFRR [SEQ ID NO:2], GGFFKR [SEQ ID NO:50], KGFFRG [SEQ ID NO:60], AVFFKR [SEQ ID NO:62], KVFFAR [SEQ ID NO:64] and KVAFKR [SEQ ID NO:63], where the peptide binds calreticulin. Preferably, the peptide is from about 6 to 100 amino acids. The invention also includes a pharmaceutical composition comprising the peptide and a pharmaceutically acceptable carrier. In a preferred embodiment, the carrier is a lipid vesicle.

The invention also includes a method of medical treatment of a patient having cancer, chronic inflammatory disease, osteoporosis or other bone disorders comprising administering using the pharmaceutical compositions described herein.

BRIEF DESCRIPTION OF DRAWINGS

FIGS. 5A–C show the effects of various peptides in reversing androgen receptor-calreticulin interactions. Androgen receptor and calreticulin were incubated in the presence of peptides and allowed to interact with an oligonucleotide containing the androgen response element. The interaction was analyzed by gel mobility shift assay. Sequences of peptide are shown in Table VI.

DETAILED DESCRIPTION OF PREFERRED EMBODIMENTS

Figure 1A:
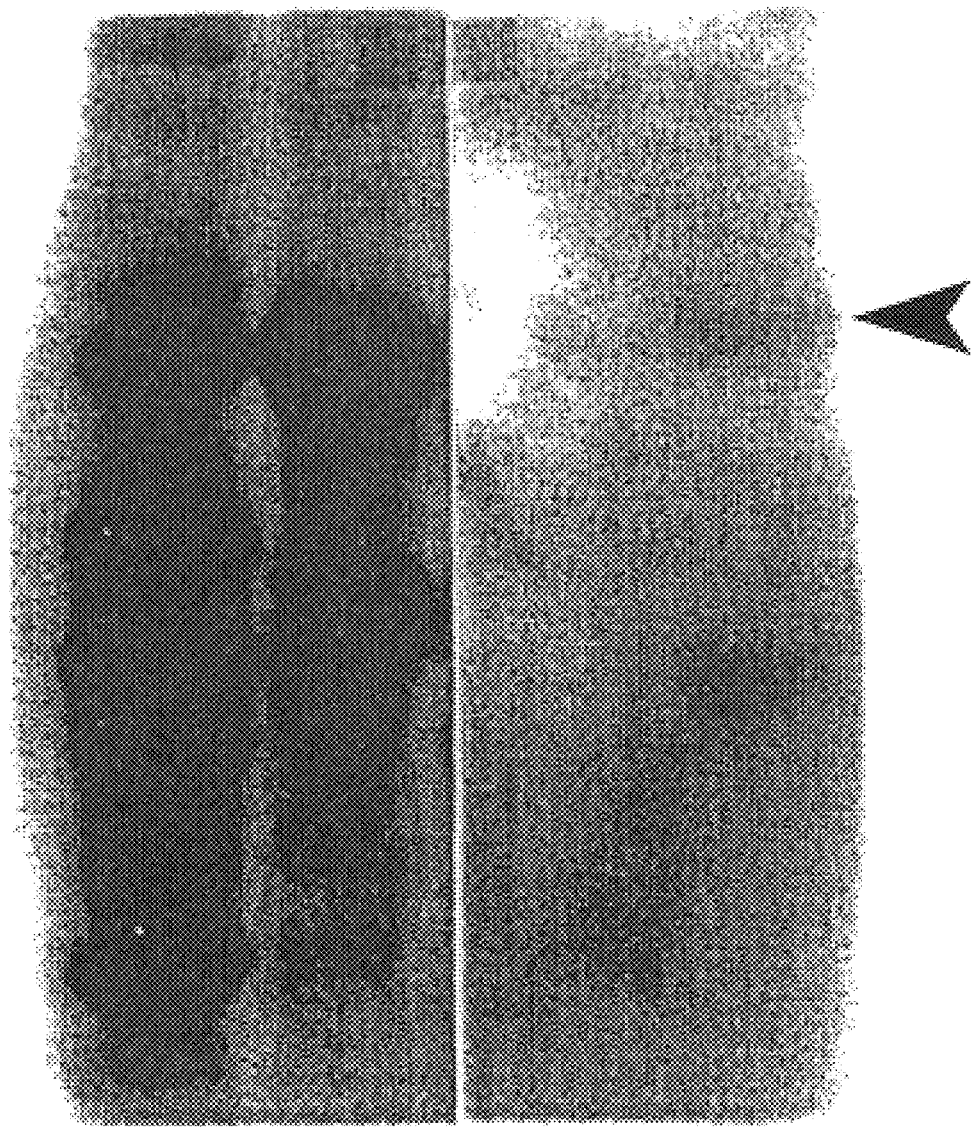
FIG. 1A shows the isolation of p60 (calreticulin) from nuclei by affinity chromatography on KLGFFKR-sepharose [SEQ ID NO:7].

A highly homologous amino acid sequence [SEQ ID NO:1], $KXFFX^1R$ (where X is either G, A or V and where $X^1$ is either K or R), has been found to be present in the DNA binding domain of all known members of the steroid hormone receptor family (Fuller, 1991), and amino acids in this sequence make direct contact with nucleotides in their DNA responsive elements, and are crucial for DNA binding (Luisi, 1991).

Naturally occurring and recombinant calreticulin, inhibit the binding of receptors to DNA. Thus, calreticulin and proteins which mimic or bind to calreticulin modulate nuclear hormone receptor regulation of gene transcription.

A By way of example, the amino acid sequence of the DNA binding domains of RAR (SEQ ID NO:8), RXR (SEQ ID NO:5), $T_3R\beta$ (SEQ ID NO:2), VDR (SEQ ID NO:2), GR (SEQ ID NO:3), MR (SEQ ID NO:3), AR (SEQ ID NO:3), ER (SEQ ID NO:4) and Integrin α subunits (SEQ ID NO:9) are set out below:

tides.with the generic sequence $KXFFX^1R$ [SEQ ID NO:1]. The inhibition of DNA binding by calreticulin can also be reversed by an antibody to or inhibitor of calreticulin. Transient or stable overexpression of calreticulin by cDNA transfection also results in the inhibition of nuclear hormone receptor induced gene transcriptional activity. Furthermore, decreased expression of calreticulin by stable transfection of antisense calreticulin cDNA results in increased sensitivity of the cells to hormones due to the increased transcriptional activity of the nuclear hormone receptor.

Hence, a proportion of nuclear hormone receptors may be occupied by calreticulin in a constitutive manner, and decreased regulation of expression of calreticulin may therefore result in an effective increase in the number of unoccupied receptors leading to increased transcriptional activity of these receptors.

By this invention, hormonal sensitivity can be manipulated by (i) increasing or decreasing the intracellular concentration of calreticulin, or (ii) by inhibiting the interaction of calreticulin with nuclear hormone receptors by peptides, peptide mirnetics, and antibodies against calreticulin, the [SEQ ID NO:1] $KXFFX^1R$ sequence or the $KGX_1X_2X_3R$ [SEQ ID NO:67] sequence.

The nuclear hormone receptors that interact with calreticulin include androgen receptor, retinoic acid receptors (RAR and RXR), glucocorticoid receptor, and the vitamin D receptor. In all of these cases, calreticulin inhibits receptor binding to DNA, and overexpression of calreticulin results in an inhibition of receptor mediated transcriptional activity. In the case of the retinoic acid receptor system, the decreased regulation of expression of calreticulin results in an increased sensitivity of the cells to differentiation by retinoic acid.

The peptides or peptide mimetics of this invention include a peptide comprising the amino acid sequence $KGX_1X_2X_3R$ where one or more of $X_1$, $X_2$ or $X_3$ is a basic amino acid [SEQ ID NO:67] and the peptide binds to calreticulin.

These peptides may be from about 6 to 100 amino acids. Peptides comprising one or more d-amino acids are contemplated. Also contemplated are peptides wherein one or

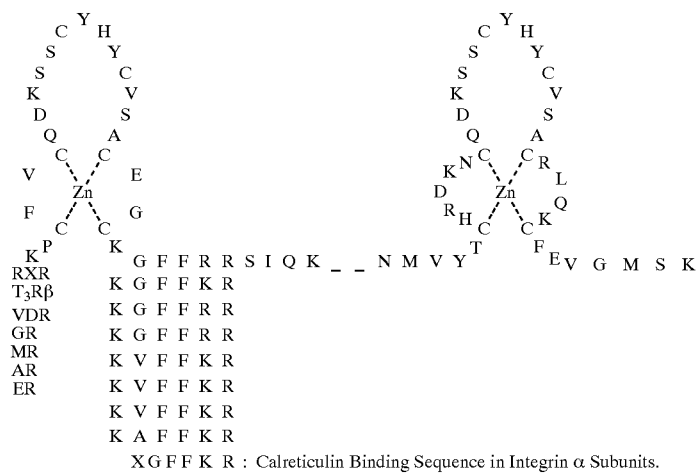

XGFFKR : Calreticulin Binding Sequence in Integrin α Subunits.

Calreticulin binds to nuclear hormone receptors by interacting with the amino acid sequence [SEQ ID NO:1] $KXFFX^1R$. The interaction results in a profound inhibition of nuclear hormone receptor DNA binding activity which can be reversed by soluble competing synthetic pepmore amino acid are acetylated at the N-terminus. Those of skill in the art recognize that a variety of techniques are available for constructing peptide mimetics with the same or similar desired biological activity as the corresponding peptide compound but with more favorable activity than the peptide with respect to solubility, stabitlity, and susceptibility to hydrolysis and proteolysis. See, for example, Morgan et al. (1989). Examples of suitable peptide mimetics for use herein are described in U.S. Pat. No. 5,643,873 which is incorporated herein by reference in its entirety.

These peptides may also be used in pharmaceutical compositions that modulate the metabolic effects of calreticulin. The peptides of this invention may be used in treatment of diseases such as breast cancer, chronic inflammatory disease and osteoporosis. The pharmaceutical compositions of this invention used to treat patients having degenerative diseases, disorders or abnormal physical states could include an acceptable carrier, auxiliary or excipient.

The pharmaceutical compositions can be administered to humans or animals by methods such as aerosol administration, direct lavage and intravenous injeciton. Dosages to be administered depend on patient needs, on the desired effect and on the chosen route of administration. The peptides may be introduced using in vivo delivery vehicles such as liposomes. They may also be introduced into these cells using physical techniques such as microinjection and electroporation or chemical methods such as coprecipitation and incorporation of DNA into liposomes.

The pharmaceutical compositions can be prepared by known methods for the preparation of pharmaceutically acceptable compositions which can be administered to patients, and such that an effective quantity of the peptides are combined in a mixture with a pharmaceutically acceptable vehicle. Suitable vehicles are described, for example in Remington's Pharmaceutical Sciences (Remington's Pharmaceutical Sciences, Mack Publishing Company, Easton, Pa., USA 1990).

On this basis, the pharmaceutical compositions could include an active compound or substance, such as a peptide of the invention, in association with one or more pharmaceutically acceptable vehicles or diluents, and contained in buffered solutions with a suitable pH and isoosmotic with the physiological fluids. The methods of combining the peptides with the vehicles or combining them with diluents is well known to those skilled in the art. The composition could include a targeting agent for the transport of the active compound to specified sites within tissue.

In vitro such peptides or vectors may be administered by infection, microinjection, electroporation and by other methods known in the art.

In vivo parenteral administration of the peptides or peptide mimetics is preferred with subdermal or intramuscular administration most preferred. Intravenous administration or use of implanted milliosmol pumps (available from Alza) may also be used.

When used for parenteral administration, which is preferred, the peptides or peptide mimetics of the present invention may be formulated in a variety of ways. Aqueous solutions of the peptide or peptide mimetics of the present invention may be encapsulated in polymeric beads, liposomes, nanoparticles or other injectable depot formulations known to those of skill in the art. (Examples thereof may be found, for example, in Remington's Pharmaceutical Sciences, 18th Edition, 1990.) Doses are selected to provide effective inhibition.

Compositions including a liquid pharmaceutically inert carrier such as water may also be considered for both parenteral and oral administration. Other pharmaceutically compatible liquids may also be used. The use of such liquids is well known to those of skill in the art. (Examples thereof may be found, for example, in Remington's Pharmaceutical Sciences, 18th Edition, 1990.)

The dose level and schedule of administration may vary depending on the particular peptide or peptide mimetic used, the method of administration, and such factors as the age and condition of the subject.

As discussed previously, parenteral administration is preferred, but formulations may also be considered for other means of administration such as orally, per rectum, and transdermally. The usefulness of these formulations may depend on the particular compound used and the particular subject receiving the compound.

Oral formulations of peptides or peptide mimetics may optionally and conveniently be used in compositions containing a pharmaceutically inert carrier, including conventional solid carriers, which are conveniently presented in tablet or capsule form. Formulations for rectal or transdermal use may contain a liquid carrier that may be oily, aqueous, emulsified or contain certain solvents suitable to the mode of administration. Suitable formulations are known to those of skill in the art. (Examples thereof may be found, for example, in Remington's Pharmaceutical Sciences, 18th Edition, 1990.)

DEFINITIONS

In this application, the following terms have the following meanings, unless the context requires otherwise:

"Binds" means that under given conditions of ionic strength and temperature, a particular product binds to a substrate "EDTA" means ethylenediaminetetraacetic acid "EGF" means Epidermal growth factor "ELISA" means enzyme-linked immunosorbent-assay "FGF" means Fibroblast growth factor "HPLC" means high performance liquid chromatography "IGF" means insulin-like growth factor "KXFFX$^1$R" [SEQ ID NO:1] means an amino acid sequence, wherein X is G, A or V and wherein X$^1$ is K or R "p60" means a 60 kDA protein, calreticulin "PAGE" means polyacrylamide gel electrophoresis "Peptide" includes amino acids, peptides, polypeptides and proteins "RXR" means retinoid X receptor "TGF-B" means Transforming growth factor—β

"VDR" means vitamin D receptor

"VDRE" means vitamin D response element

The amino acids which comprise the various amino acid sequence appearing herein may be identified according to the following one letter abbreviations:

| AMINO ACID | ONE LETTER ABBREVIATION |
|---|---|
| Alanine | A |
| Arginine | R |
| Asparagine | N |
| Aspartic Acid | D |
| Cysteine | C |
| Glutamine | Q |
| Glutamic Acid | E |
| Glycine | G |
| Histidine | H |
| Isoleucine | I |
| Leucine | L |
| Lysine | K |
| Methionine | M |
| Phenylalanine | F |
| Proline | P |
| Serine | S |
| Threonine | T |

-continued

| AMINO ACID | ONE LETTER ABBREVIATION |
|---|---|
| Typtophan | W |
| Tyrosine | Y |
| Valine | V |

EXAMPLES

Except whether otherwise indicated in the following examples, cell lines were obtained from American Type Culture Collection—ATCC; Chemical reagents were purchased from Sigma Chemicals, St. Louis, Mo.; BioRad, Richmond, Calif.; and Amersham Corp., Oakville, ON; Radioisotopes were purchased from Amersham Corp., Oakville, ON; Peptides were synthesized by HSC/Pharmacia Biotechnology Service and Department of Clinical Biochemistry, University of Toronto; Oligonucleotides were synthesized by University of Toronto—Carbohydrate Research Group; Centrifuges used were from Beckman or Eppendorf.

Example 1

Calreticulin is Present in Nucleus of Cells

The conservation of the $KX^2GFFX^3R$ sequence [SEQ ID NO:10] in the α-subunits of integrins is shown in Table I.

A computer search of the Swiss protein data bank for the presence of this sequence motif in other proteins revealed that a highly homologous sequence is present in the DNA binding domain of all members of the nuclear hormone receptors (Table 1) (Fuller, 1991; Carson-Jurica, et al., 1990). Because amino acids in this motif have been demonstrated to be essential for the binding of nuclear hormone receptors to their DNA responsive elements (Luisi et al., 1991; Hard et al., 1990), we wanted to determine whether a 60 kDa protein isolated by affinity chromatography on a KLGFFKR-sepharose affinity matrix (Rojiani et al., 1991) could modulate DNA binding and transcriptional activities of nuclear hormone receptors.

coid receptor; MR: Minerolcorticoid receptor; AR: Androgen receptor; PR: Progesterone receptor; ER: Estrogen receptor.

Although calreticulin contains a KDEL motif at its C-terminus and is therefore thought to be resident in the endoplasmic reticulum (McCauliffe et al., 1990; Fliegel et al., 1989; Michalak et al., 1992), it also has a nuclear targeting .:signal (McCauliffe et al., 1990; Michalak et al., 1992; Marzluff et al., 1985), raising the possibility that this protein is also present in the nucleus (Michalak et al., 1992). The presence of p60 in nuclei was demonstrated by affinity chromatography of human osteosarcoma cell (HOS) nuclear extracts on a KLGFFKR-affinity column [SEQ ID NO:7] (FIG. 1).

Nuclei were purified from HOS cells by established methods (Luisi et al., 1991). The purified nuclei were either lysed in PBS containing 1 % Triton X-100, 0.1% SDS, 0.5% sodium deoxycholate and 1 mM PMSF, or were applied to a glass coverslip and stained for nuclear antigen with anti-nuclear monoclonal antibody MAB1218 obtained from Chemicon Int. Inc., Tamecula, Calif. The nuclei were visualized by indirect immunofluorescence. The total cellular or nuclear extracts were subjected to affinity chromatography on a KLGFFKR-affinity matrix [SEQ ID NO:7], and the p60 isolated (Rojiani et al., 1991).

Cell extracts were prepared from whole cells or from purified nuclei and applied to KLGFFKR-sepharose affinity matrix [SEQ ID NO:7]. Bound proteins were eluted with EDTA and analyzed by SDS-polyacrylamide gel electrophoresis (Rojiani et al., 1991). The separated proteins were electrophoretically transferred to nitrocellulose filters and probed with an anti-calreticulin antibody. In FIG. 1, Lane 1: Total cellular extract; Lane 2: EDTA eluted material from affinity column to which total cellular extract was applied; Lane 3: Nuclear extract; Lane 4: EDTA eluted material from affinity column to which nuclear extract was applied. Arrow indicates the position of p60.

Figure 1B:
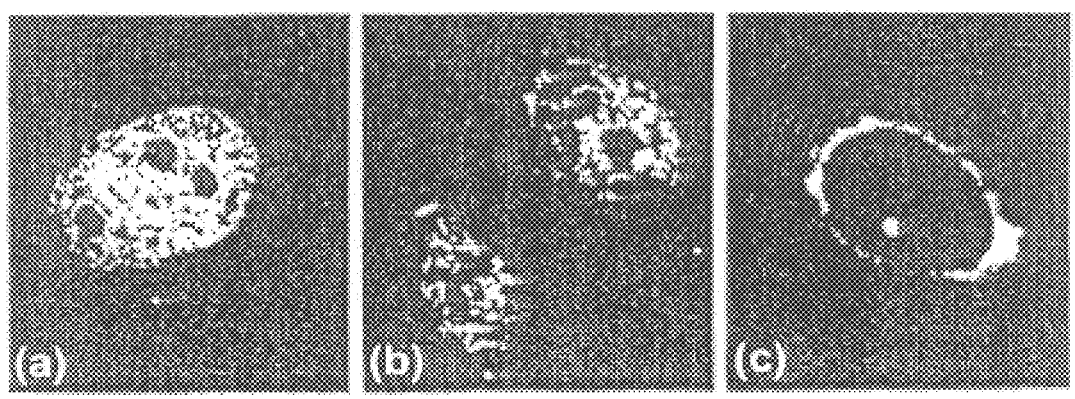
FIG. 1B shows immunofluorescent confocal images of TE-85 human osteosarcoma cell nuclei stained with an antibody against calreticulin (panels a, b and c show different cells).

Indirect immunofluorescence of HOS cells or purified nuclei with anti-calreticulin antibody also demonstrated intranuclear calreticulin expression, as shown in FIG. 1B. Confocal microscopy was carried out using a BioRad MRC

TABLE I

Conservation of an Amino Acid Sequence Motif in the Integrin Alpha-subunit Cytoplasmic Domains and in the Steroid Hormone Receptor Family

| | Integrins* | | | Steroid Nuclear Receptors | |
|---|---|---|---|---|---|
| a1 | KIGFFKR | [SEQ ID NO:11] | RARa | ACEGCKGFFRRSIQK | [SEQ ID NO:18] |
| a2 | KLGFFKR | [SEQ ID NO:7] | T₃Rb | TCEGCKGFFRRTIQK | [SEQ ID NO:19] |
| a3 | KCGFFKR | [SEQ ID NO:12] | VDR | TCEGCKGFFRRSMKR | [SEQ ID NO:20] |
| a4 | KAGFFKR | [SEQ ID NO:13] | GR | TCGSCKVFFKRAVEG | [SEQ ID NO:21] |
| a5 | KLGFFKR | [SEQ ID NO:7] | MR | TCGSCKVFFKRAVEG | [SEQ ID NO:21] |
| a6 (A) | KCGFFKR | [SEQ ID NO:12] | AR | TCGSCKVFFKRAAAG | [SEQ ID NO:22] |
| a6 (B) | KCGFFKR | [SEQ ID NO:12] | PR | TCGSCKVFFKRAMEG | [SEQ ID NO:23] |
| a7 | KLGFFKR | [SEQ ID NO:7] | ER | SCEGCKAFFKRSIQG | [SEQ ID NO:24] |
| a8 (chick) | KCGFFDR | [SEQ ID NO:14] | RXR | SCEGCKGFFKRTVRK | [SEQ ID NO:25] |
| av | RMGFFKR | [SEQ ID NO:15] | Steroid receptor TR2 | TCEGCTGFFKRSIRK | [SEQ ID NO:26] |
| Mac-1 | KLGFFKR | [SEQ ID NO:7] | Nerve growth factor induced protein 1-B | TCEGCKGFFKRTVQK | [SEQ ID NO:27] |
| p150 | KVGFFKR | [SEQ ID NO:16] | Early response PROTEIN nak1 | TCEGCKGFFKRTVQK | [SEQ ID NO:27] |
| PS2 (Drosophila) | KCGFFNR | [SEQ ID NO:17] | Chorion Factor 1 | SCEGCKGFFKRTVRK | [SEQ ID NO:25] |

In Table I, the sequences indicated with an asterisk were obtained as described in Rojiani et al, 1991. GR: Glucorti- 500 system. Note the non-nucleolar, intranuclear staining of the cell in (a) and (b), and the complete exclusion of intranuclear staining in the cell in (c). These data suggest that the expression of calreticulin in the nucleus is a regulated process.

These results confirmed the presence of a calreticulin-related p60 protein in nuclei.

Example 2
The Sequence KXFFX[1]R [SEQ ID NO: 1] is Present in All Known Members of the Nuclear Receptor Family As shown in Table I, the sequence KXFFX[1]R [SEQ ID NO:1] is present in all known members of the nuclear receptor family. The region containing this sequence in the DNA-binding domains of these receptors has been shown to play a crucial role in DNA sequence recognition (Luisi et al., 1991). Thus calreticulin, by binding to this common sequence, modulates the binding of all members of the receptor family to DNA. By way of example, we have demonstrated the inhibition by calreticulin of the interaction of the androgen receptor with its DNA response element (see Examples 3 and 4) and of the retinoic acid receptor heterodimer complex (RAR/RXR) with its DNA response element (see Example 5).

Example 3
Ability of Calreticulin to Modulate Binding of Nuclear Hormone Receptors In Vitro To determine whether p60 (calreticulin) could directly modulate the binding of nuclear hormone receptors to DNA via the KXFFX[1]R [SEQ ID NO:1] sequence, the interaction of the DNA binding domain of recombinant androgen receptor with its hormone responsive element was analyzed by carrying out gel mobility shift assays.

As described in Rennie et al., 1993, DNA binding domain of recombinant rat androgen receptor was prepared as a GST-fusion protein using the pGEX-3X vector and purified by glutathione-agarose affinity chromatography. p60 (calreticulin) was purified by affinity chromatography on KLGFFKR-sepharose [SEQ ID NO:7], followed by gel electrophoresis as described in detail in Rojiani et al., 1991. Purified AR and p60 (calreticulin) were found to be greater than 90% and 95% pure, respectively, as determined by SDS-PAGE and Coomassie Blue staining. Recombinant calreticulin (GST-fusion protein) was prepared as described by Baksh and Michalak, 1991. Gel retardation assays were carried out as described by Rennie et al., 1993. To analyze the effect of p60, or recombinant calreticulin, on receptor-DNA binding activity, the AR was pre-incubated with p60 for 30 min at 4° C. To analyze the effects of synthetic peptides, anti-calreticulin antibody, and non-immune IgG on p60 inhibition of AR-ARE binding, the peptide, antibody or IgG were pre-incubated with p60 for 30 min at 4° C. The androgen receptor preparation was then added to these mixtures and further incubated for 30 min at 4° C.

Affinity purified DNA binding domain of the recombinant rat androgen receptor (AR) was pre-incubated with or without the indicated concentrations of purified p60 at 4° C. for 30 min. After this pre-incubation the reaction mixtures were incubated with $^{32}$P-labeled 26 base pair ARE (Rennie et al., 1993) (androgen response element), and analyzed by gel retardation assay. The sequence of the ARE used was [SEQ ID NO:28]:

5' GTAAAGTACTCCAAGAACCTATTTgt 3'

3' CATTTCATGAGGTTCTTGGATAAAca 5'

Figure 2A:
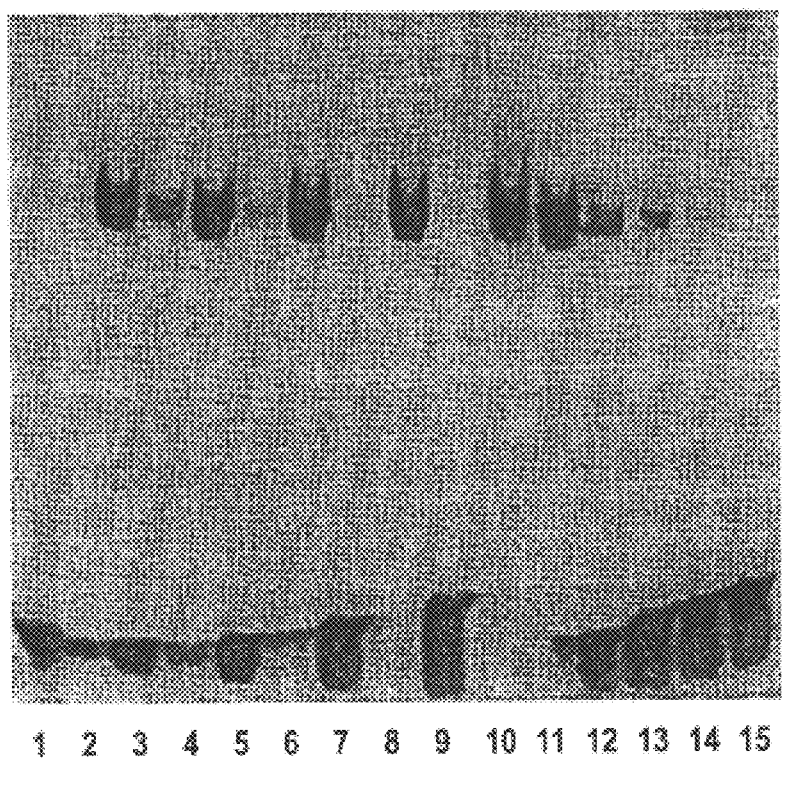
FIG. 2A shows that preincubation of purified p60 (calreticulin) with the recombinant receptor resulted in a dose-dependent inhibition in the formation of the complex between the receptor and the DNA.

In FIG. 2A, the following lanes show the following results: Lane 1 $^{32}$P-labeled ARE by itself; Lane 2: Retardation of ARE by AR; Lane 3: Effect of pre-incubation of 0.11 μg of purified p60 with AR on AR-ARE binding; Lane 4: Effect of the addition of a 25-fold molar excess of KLGFFKR synthetic peptide [SEQ ID NO:7] to p60 on AR-ARE binding. Lanes 3, 5, 7, & 9: Effect of increasing concentrations of p60 (from 0.11 μg to 0.33 μg) on AR-ARE binding; Lanes 4, 6, 8, & 10: Reversal of p60 inhibition of AR-ARE binding by KLGFFKR peptide [SEQ ID NO:7]. Lane 11: Effect of addition of anti-calreticulin antibody to p60 inhibition of AR-ARE binding. Lanes 12–15: Increasing amounts of p60 in the presence of anti-calreticulin antibody. Increasing the p60 concentration overcomes the effect of antibody on p60 inhibition of AR-ARE.

Figure 2B:
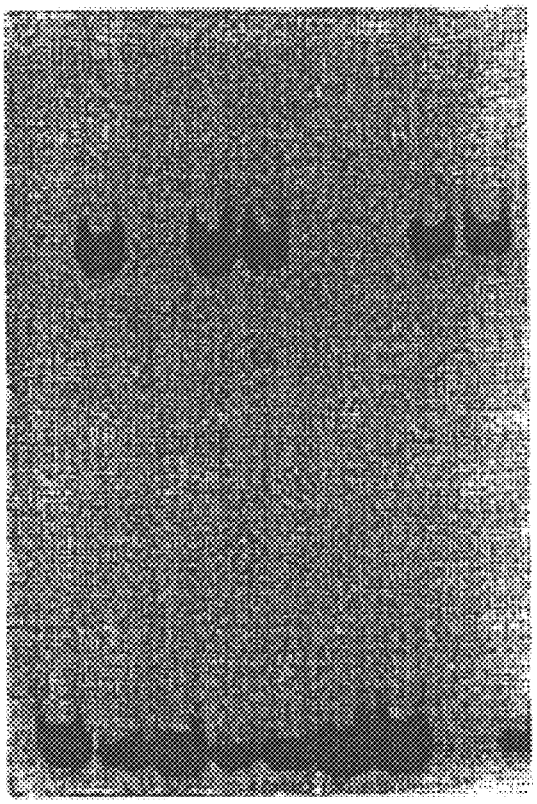
FIG. 2B shows that recombinant calreticulin inhibits the binding of the androgen-receptor to its response element.

In FIG. 2B, the following lanes show the following results: Lane 1: $^{32}$P-labelled ARE alone; Lane 2: Retardation of ARE by AR in the presence of glutathione-S-transferase (GST); Lane 3: Inhibition by GST-calreticulin (GST-calreticulin) of AR-ARE interaction; Lanes 4 and 5: Reversal of this inhibition by KLGFFKR peptide [SEQ ID NO:7]; Lanes 6 and 7: Inability of the scrambled peptide (KLRFGFK) [SEQ ID NO:29] in reversing the effect of calreticulin on AR-ARE interaction; Lanes 8 and 9: The peptide KVFFKR [SEQ ID NO:3] can also reverse the inhibition by calreticulin of the AR-ARE interaction. The concentration of calreticulin used was 2 μg and the peptides were used at a 50-fold molar excess concentration.

As shown in FIG. 2, the migration of a $^{32}$P-labeled 26 base pair DNA androgen responsive element residing at positions –115 to –140 of the rat probasin gene promoter (Rennie et al., 1993) was retarded by the androgen receptor DNA-binding domain; indicating the formation of a complex between the receptor and the DNA (Rennie et al., 1993). Pre-incubation of purified p60 (calreticulin) with the recombinant receptor resulted in a dose-dependent inhibition in the formation of this complex (FIG. 2A, lanes 3, 5, 7, & 9). The sequence specificity of this inhibition was demonstrated by the finding that the inhibition by p60 (calreticulin) of receptor-DNA binding was reversed by the addition of competing KLGFFKR peptide [SEQ ID NO:7] (FIG. 2A, lanes 4, 6, 8, & 10) or KVFFKR [SEQ ID NO:3] (FIG. 2B, lanes 8 and 9), whereas a scrambled peptide (KLRFGFK) [SEQ ID NO:29] was much less effective (FIG. 2B, lanes 6 and 7). An antibody to calreticulin, which cross-reacts with p60, also reversed this inhibition by p60 (FIG. 2A, lane 11), demonstrating p60 specificity. Non-immune IgG did not have any effect on the inhibition of receptor-DNA interaction by p60 (FIG. 2A, lane 15). Furthermore, neither KLGFFKR peptide [SEQ ID NO:7], anti-calreticulin antibody, nor non-immune IgG by themselves had any effect on the receptor-DNA interaction (data not shown). p60 did not effect the binding of AP-1 to DNA, and other proteins of similar size (e.g. bovine serum albumin) also did not have any effect on the nuclear receptor-DNA interaction.

Recombinant calreticulin (obtained from Dr. Michalak, Edmonton, Alta) (Baksh et al., 1991), in the form of a GST-fusion protein, also inhibited the binding of the androgen-receptor to its response element (FIG. 2B, lane 2), and this inhibition was also reversed by KVFFKR peptide [SEQ ID NO:3], (FIG. 2B, lane 2), but not by a scrambled peptide KLRFGFK [SEQ ID NO:29] (FIG. 2B, lane 1) confirming that the p60 purified on the KLGFFKR [SEQ ID NO:7] affinity matrix and calreticulin are functionally similar in terms of binding to nuclear hormone receptors, and that a synthetic peptide, KVFFKR [SEQ ID NO:3] can competitively inhibit the binding of calreticulin to the KVFFKR [SEQ ID NO:3] sequence of the androgen receptor.

Example 4
Inhibition of Transcriptional Activity of the Androgen Receptor In Vivo To determine whether calreticulin also inhibited the transcriptional activity of the androgen receptor in vivo, expression vectors containing full-length calreticulin (McCauliffe et al., 1990) and androgen receptor (Rennie et al., 1993), cDNAs were co-transfected into Vero fibroblasts together with a chloramphenicol acetyl transferase (CAT) reporter plasmid driven by the mouse mammary tumor virus (MMTV) long terminal repeat (LTR). MMTV-LTR contains androgen response elements (Rennie et al., 1993).

Figure 2C:
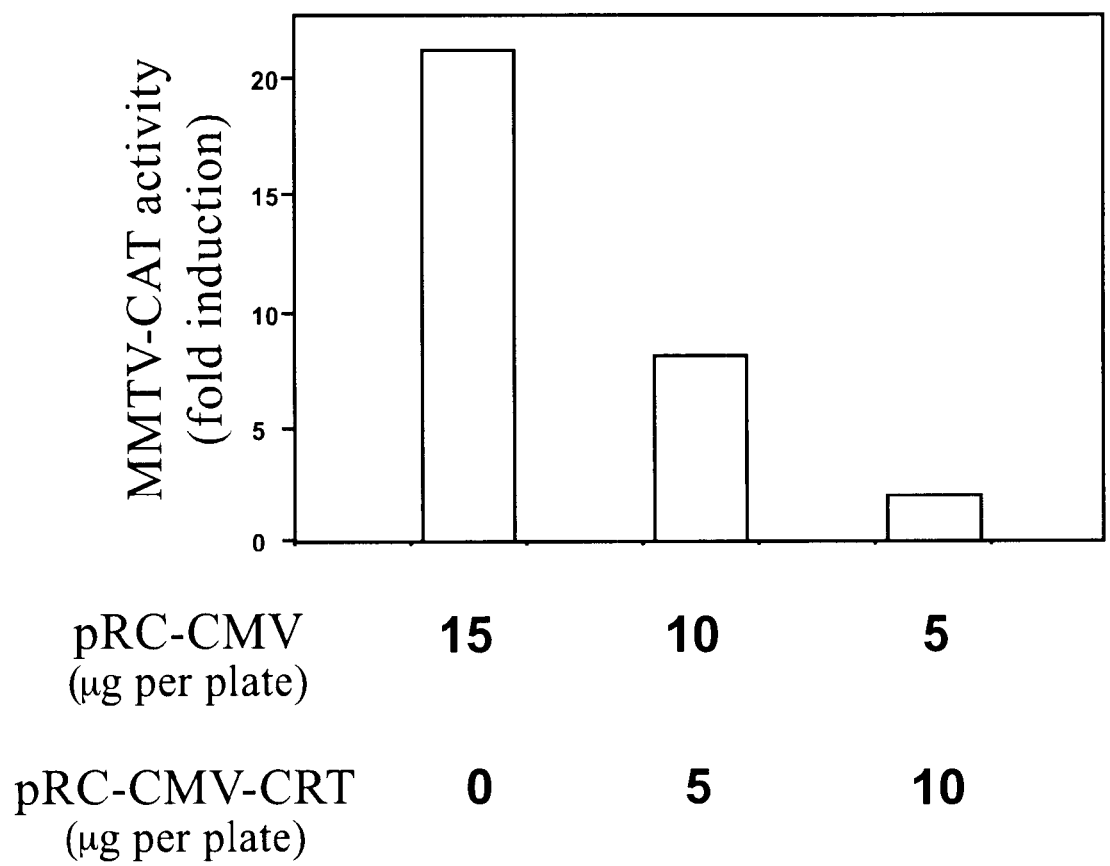
FIG. 2C shows that co-transfection of the calreticulin-containing plasmid resulted in a dose-dependent inhibition of chloramphenicol acetyltransferase activity induced by the androgen receptor.

FIG. 2C shows inhibition of androgen-induced CAT activity by calreticulin. Vero fibroblasts were cotransfected with an MMTV-CAT reporter vector and various amounts of a calreticulin expression vector and the pRC-CMV vector alone (Invitrogen) using the calcium phosphate method (Filmus et al., 1992). In all transfections 10 µg of a β-galactosidase expression vector and 10 µg of an androgen receptor expression vector (Seed et al., 1988) were included. Transfected cells were incubated in medium alone or in the presence of 100 nM R1881 (synthetic androgen) for 12 h. Cells were then lysed and CAT activity measured (Seed et al., 1988). An aliquot of the cell extracts was also assayed for β-galactosidase activity. This activity was used to standardize the measurement of CAT levels in each experiment by taking into account the efficiency of the transfection. Every sample was tested in quadruplicate and the average activity calculated. CAT activity induction as defined as the ratio between the standardized CAT activity of the R1881 treated cells and the corresponding untreated cultures. The Vero cells were grown in a-minimum essential medium containing 10% charcoal-treated calf serum.

As shown in FIG. 2C, co-transfection of the calreticulin containing plasmid resulted in a dose dependent inhibition of CAT activity induced by the androgen receptor. Furthermore, immunoprecipitation of calreticulin from $^{35}$S-methionine/cysteine labeled, androgen receptor transfected Vero cells, resulted in the co-precipitation of the 110 kDa androgen receptor, indicating a direct interaction between calreticulin and the androgen receptor.

These data demonstrate that not only can calreticulin bind to the androgen receptor DNA binding domain and inhibit its interaction with the androgen response elements in vitro, it can also inhibit the transcriptional activity of the androgen receptor in vivo. Although other 59 kDa proteins have been found in complexes with several steroid hormone receptors (Lebeau et al., 1992; Tai et al., 1992), they are distinct from calreticulin, and none of them have an effect on binding of the receptors to their DNA responsive elements.

Modulation of PSA Secretion by Androgen Responsive LnCap Cells

The cells were treated either with tissue culture medium (TCM) alone, TCM containing the synthetic androgen, R1881 or the androgen receptor derived peptide KVFFDR [SEQ ID NO:3], or both. After overnight incubations, PSA was measured in conditioned medium by radioimmunoassay.

Example 5
Regulation by Calreticulin of Hormone Receptor Induced Gene Transcription In order to demonstrate a physiological significance to the finding that calreticulin can bind to the DNA binding domain of nuclear hormone receptors and modulate their transcriptional activity, we utilized a retinoic acid responsive system i.e. the induction of neuronal differentiation by retinoic acid in P19 embryonal carcinoma cells (McBurney et al., 1982). We predicted that increased expression of calreticulin would suppress retinoic acid induced neuronal differentiation, whereas decreased expression would result in the release of calreticulin inhibition, and allow for a more rapid rate of neuronal differentiation.

The full length 1.9 Kb calreticulin cDNA (McCauliffe et al., 1990) was obtained from Dr. R. D. Sontheimer, Texas and was subcloned into pRC/CMV (Invitrogen, San Diego, Calif.) expression vector in the sense and antisense orientation. pRC/CMV, pRC/CMV-Cal-1 (sense), or pRC/CMV-Cal-2 (antisense) expression plasmids were then transfected into P19 embryonal carcinoma cells by electroporation. Neomycin-resistant transfectant cells were then selected by growth in the presence of 600 µg/ml G418 and the resistant cells were maintained in 100 µg/ml G-418. Cal-1 and Cal-2 transfectants were subcloned by limiting dilution, and the subclones were screened for calreticulin expression by Western blot analysis of cell lysates with an anti-calreticulin antibody (Rojiani et al., 1991).

Retinoic acid neuronal differentiation was induced as described previously (McBurney et al., 1982; Dedhar et al., 1991) and class III β-tubulin expression was analyzed by Western blotting with a class III β-tubulin monoclonal antibody (TuJ1). This antibody was obtained from Dr. A. Frankfurter, University of Virginia, Charlottesville, Va., USA. The bRARE-luciferase transient transfections in p19 (Neo), Cal-1 and Cal-2 cells were carried out as described in Tini et al., 1993. The vector bRARE(3) tk-LUC was constructed by linking 3 copies of the 32 base pair sequence that defines the RARE upstream from the RAR-b gene (de The, et al., 1990; Sucov et al., 1990) to the minimal thymidine kinase promoter and the firefly luciferase gene.

The level of calreticulin expression was estimated by Western blot analysis of cellular lysates (Rojiani et al., 1991) followed by densitometric scanning. For Northern blot analysis total cellular RNA (15 µg) from the indicated cell lines was hybridized to $^{32}$-P-labeled CRABP(II) cDNA (Giguere et al., 1990) at 65° C. using Rapid Hyb buffer (Amersham Corp.). The blot was stripped and reprobed with a mouse actin cDNA probe to check for equal loading of RNA. Values for relative mRNA levels were derived from quantitation of the signal in each lane using a Molecular Dynamics Phosphorimager. CRABPII mRNA levels were normalized against the corresponding actin mRNA signal.

The level of expression of calreticulin was modulated in P19 EC cells by transfection with calreticulin cDNA inserted in the sense or antisense orientation in the pRC/CMV (Invitrogen Corp., San Diego, Calif.) expression vector. P19 EC cell subclones overexpressing calreticulin (Cal-1), or anti-sense transfectants with reduced calreticulin expression (Cal-2), as well as control transfected cells (Neo), were subjected to induction of neuronal differentiation by retinoic acid as described previously (McBurney et al., 1982; Dedhar et al., 1991). The expression of neuron-specific class III β-tubulin (Lee et al., 1990; Alexander et al., 1991) was then analyzed 48 hr (A) or 72 hr (B) after the addition of all-trans retinoic acid (5 mM). Cal-1 (1A2 and 1D2) clones were transfected with pRC/CMV containing calreticulin cDNA in the sense orientation. Cal-2 (1A4 and 1B4) clones were transfected with pRC/CMV containing calreticulin cDNA in the anti-sense orientation. (C): Effect of levels of calreticulin expression on retinoic acid mediated neuronal differentiation.

Cells were stained with anti-class III β tubulin antibody (TuJi) followed by FITC conjugated secondary antibody as described above. A and B: P19 (neo) EC cells; C and D: P19-Cal-1 EC cells; E and F: P19 Cal-2 EC cells. A, C and E; untreated cells. B, D and F: 6 days at RA (0.5 μM) treated cells. The cells were visualized using a Zeiss Axioscop microscope under oil immersion and photographed with Kodak T-Max 400 film. Magnification 100×.

Figure 3A:
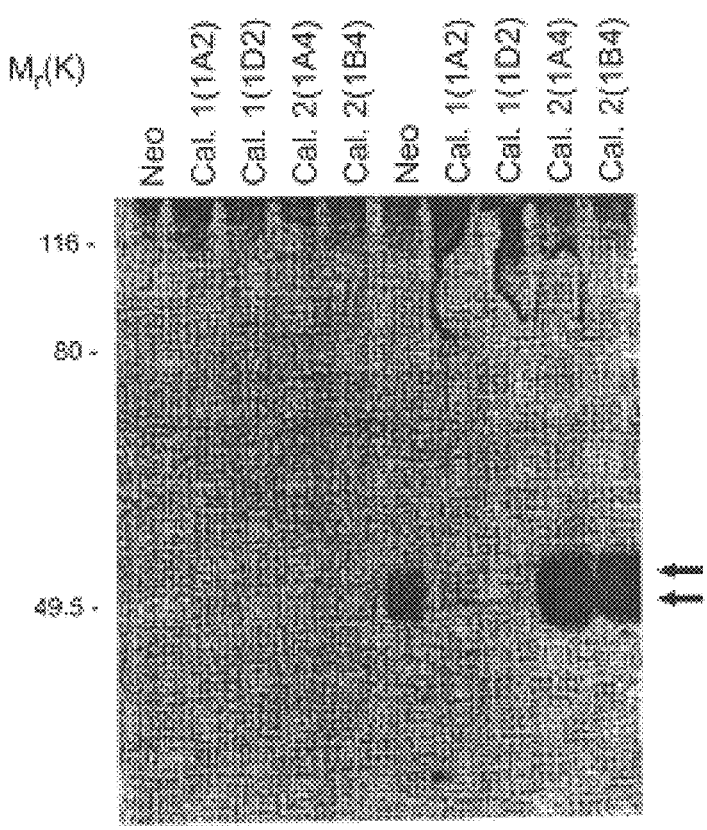
FIG. 3A shows that overexpression of calreticulin by calreticulin cDNA transfection in p19EC cells dramatically suppressed neuronal differentiation, as judged by the expression of a specific early marker of neuronal differentiation class III β-tubulin.
Figure 3B:
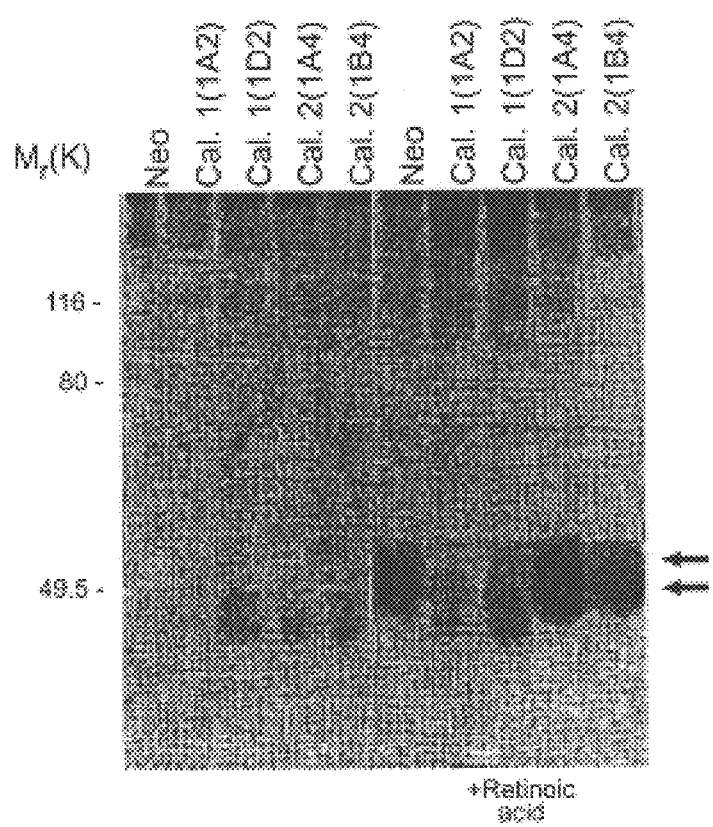
FIG. 3B shows that overexpression of calreticulin by calreticulin cDNA transfection in p19EC cells dramatically suppressed neuronal differentiation, as judged by the expression of a specific early marker of neuronal differentiation class III β-tubulin.

As shown in FIG. 3A and B, overexpression of calreticulin (Cal-1), by calreticulin cDNA transfection in P19 EC cells indeed dramatically suppressed neuronal differentiation, as judged by the expression of a specific early marker of neuronal differentiation, class III β-tubulin (Lee et al., 1990; Alexander et al., 1991). In contrast, decreased expression of calreticulin (Cal-2), by anti-sense calreticulin cDNA transfection, resulted in markedly enhanced expression of class III β-tubulin.

Figure 3C:
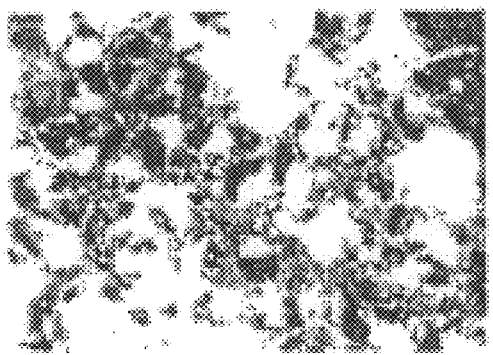
FIG. 3C shows the modulation of neuronal differentiation of P19EC cells by different levels of expression of calreticulin: (A) shows untreated P19 (neo) EC cells; (B) shows treated P19 (neo) EC cells; (C) shows untreated P19-Cal-1 EC cells; (D) shows treated P19-Cal-1 EC cells and that increased levels of calreticulin inhibit neuronal differentiation; (E) shows untreated P19 Cal-2 EC cells; and (F) shows treated P19 Cal-2 EC cells and that decreased levels of calreticulin enhance neuronal differentiation (F) shows the decreased levels of calreticulin enhance neuronal differentiation.
Figure 3C:
Figure 3C:
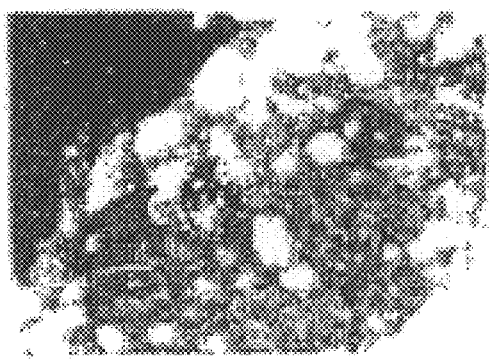
Figure 3C:
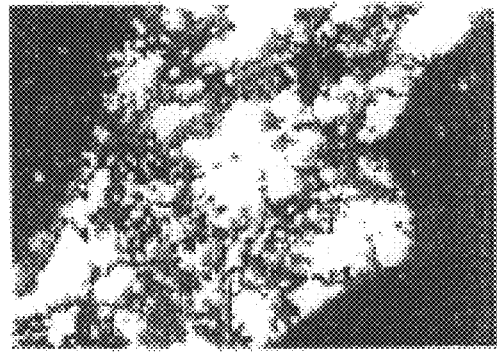
Figure 3C:
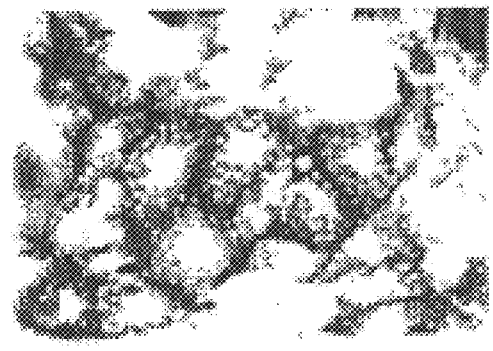
Figure 3C:
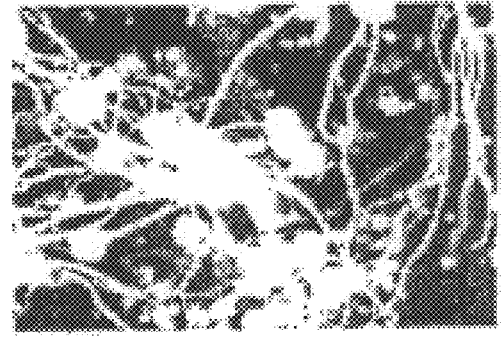

FIG. 3C clearly shows the inhibition of neuronal differentiation by calreticulin overexpression and enhanced differentiation by diminished calreticulin expression.

The effect of calreticulin levels on retinoic acid induced neuronal differentiation occurs via the direct regulation of retinoic acid responsive genes, as demonstrated by an inverse relationship between calreticulin expression level and RARE-driven luciferase gene expression (Dedhar et al., 1994). Furthermore, the endogenous regulation of expression of the retinoic acid responsive genes, CRABPII (Giguere et al., 1990) and RAR-b (de The, et al., 1990; Sucov et al., 1990) are substantially decreased in Cal-1 transfectants, but are either unchanged or slightly increased in the calreticulin-antisense Cal-2 transfectants (Dedhar et al., 1994).

Collectively, these results demonstrate that calreticulin, by binding to the conserved KXFFX$^1$R [SEQ ID NO:1] sequence in the DNA binding domain of nuclear hormone receptors (Table I), can modulate gene expression and cellular phenotypes, such as cell differentiation. Calreticulin may also behave as a signal modifier by translocating between the nucleus and the cytoplasm, where it has been shown to bind, via an identical sequence motif, to the intracellular domains of the α-subunits of integrin receptors (Rojiani et al., 1991).

Example 6
KLGFFKR [SEQ ID NO:7] Modulates Retinoic Acid Induced Gene Transcription In Vivo In order to test whether a peptide based on the calreticulin-binding KXGFFKR [SEQ ID NO:30] sequence modulates retinoic acid induced gene transcription in live cells, the p19 cells were transfected with a reporter vector consisting of a retinoic acid response element fused to the luciferase gene. Since these cells contain endogenous retinoic acid receptors RAR and RXR, treatment with retinoic acid resulted in an induction of the RARE driven luciferase activity (see FIG. 4).

Cell culture conditions: Mouse embryonic carcinoma (P19) cell, grown in 60 mm dishes in 7.5% donor calf serum, 2.5% fetal calf serum alpha MEM (Gibco/BRL) were treated with the peptides KLGFFKR [SEQ ID NO:7] or KLRFGFK [SEQ ID NO:29] for three hours or overnight for 20 hours at 37° C., 5% $CO_2$. With few exceptions, KLXFFKR [SEQ ID NO:31] is the peptide sequence specific within the binding domain of all steroid receptors. KLRFGFK [SEQ ID NO:29] is the scrambled peptide of the above sequence. Subsequently each plate was washed four times with serum free alpha MEM to remove excess peptides and replenished with fresh serum containing media. Cells were then transfected by standard calcium phosphate precipitation method (*Current Protocols in Molecular Biology* 9:1) with 1 microgram bRARE in pTKluc, 1.5 microgram pRSV bgal, 3 microgram pKS (carrier) per 60 mm dish. Following a 16 hour incubation at 37° C. 5% $CO_2$, each plate was washed two times with serum free alphaMEM and replenished with serum containing media supplement with $10^7$ M retinoic acid (Sigma R2625) and 800 microgram/ml G418 (Gibco 1181-031). Following another 24 hours incubation cells were washed three times with PBS and each 60 mm dish of cells was lysed in 100 microliters of 1 % triton X100, 100 mM $KPO_4$ pH7.8, 1 mM DTT. Cell lysates were stored at −70° C. Prior to luciferase/bgal assays, cell debris were spun out on an Eppendorf microfuge (5415C) at 4° C. full speed for 20 minutes.

Luciferase assay: All reagents were equilibrated to room temperature and each sample was assayed independently. Ten microliters of cell lysate was incubated with 50 microliters of luciferase reagent (Promega E1483) in an Eppendorf tube. Thirty seconds later, the sample was immediately counted in a Beckman scintillation counter (LS6000IC) for one minute using an open window. Standards in the range of 0.001 nanogram to 1.0 nanogram was used to establish the linearity of the assay.

Beta-gal assay: Assay was done in a microtitre plate (Linbro 76-232-05). Ten microliters of cell lysate were mixed with 90 microliters of bgal reagent in 88 mM phosphate buffer, 11 mM KCl, 1 mM $MgCl_2$, 55 mM 2ME, 4.4 mM chlorophenol red b-D-galactopyranoside (BMC 884-308). Incubation period varied from 30 minutes to 2 hours at 37° C. Results were read at 570 nm in an ELISA reader (Dynatech MR5000).

Figure 4:
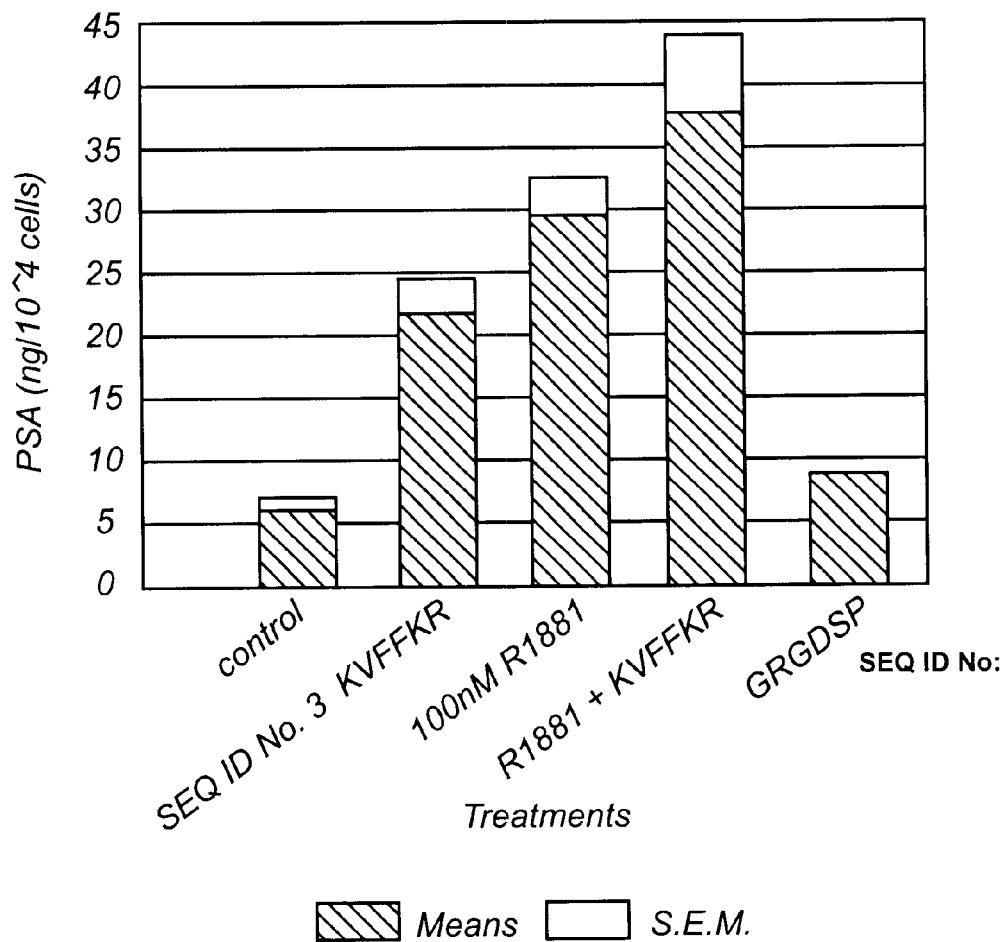
FIG. 4 shows the effects of peptides on prostate specific antigen secretion by LnCap cells in vitro.

The pre-incubation of these cells with the specific KLGFFKR peptide [SEQ ID NO:7] resulted in a dose-dependent increase in luciferase activity indicating a stimulation of the retinoic acid receptor mediated gene transcription (FIG. 4).

Similarly, a peptide which inhibited calreticulin androgen receptor interaction modulated the differentiation state of prostate cancer cells (LnCap cell line) (FIG. 4). The differentiation marker used was PSA (prostatic specific antigen). The peptide alone, when added to those cells, induced PSA which was normally induced by androgens. When added together with a synthetic androgen (R1881) the peptide enhanced PSA expression. The experiment shows the feasibility of the peptide based therapeutic approach.

These results show that peptides based on the KXFFX$^1$R [SEQ ID NO:1] sequence can be used to modulate hormone responsiveness by influencing the binding of calreticulin to the hormone receptors in live cells. Thus in the experiments described, peptides were able to effectively compete for calreticulin binding with the KGFFRR sequence [SEQ ID NO:2] in the retinoic acid or androgen receptor. This activated the calreticulin-bound receptors resulting in increased transcriptional activity.

TABLE II

OVERNIGHT INCUBATIONS

| Preincubations | [SEQ ID NO.:] | Concentrations micromolar | Luciferase x $10^6$ | Beta-gal | Corrected values luc/bgal |
|---|---|---|---|---|---|
| KLGFFKR | [SEQ ID NO:7] | 10 | 13 | 0.395 | 32.91 |
| KLGFFKR | [SEQ ID NO:7] | 50 | 20 | 0.443 | 45.15 |
| KLGFFKR | [SEQ ID NO:7] | 100 | 28 | 0.452 | 61.95 |
| KLRFGFK | [SEQ ID NO:29] | 10 | 14 | 0.333 | 42.04 |
| KLRFGFK | [SEQ ID NO:29] | 50 | 16 | 0.387 | 41.34 |
| KLRFGFK | [SEQ ID NO:29] | 100 | 14 | 0.434 | 32.26 |
| Controls | | | | | |
| no retinoic acid | | 0 | 0.17 | 0.348 | 0.49 |
| $10^{-7}$ retinoic acid | | 0 | 8.3 | 0.323 | 25.7 |

Example 7
Peptides Having Differential Specificities for Disrupting Different Hormone Receptor-Calreticulin Interactions To identify peptides having different specificities, we utilized gel mobility shift assays (see Example 3) in which known concentrations of purified recombinant androgen receptor, estrogen receptor, retinoic acid receptors (RAR/RXR and RXR/RXR) (Shago et al., 1994) and vitamin D receptor (Xu et al., 1993) were incubated with known concentrations of either recombinant calreticulin, or calreticulin purified by affinity chromatography on a KLGFFKR affinity column [SEQ ID NO:7] (see Example 3) in the presence of the respective $^{32}$P-labelled DNA response elements and known concentrations of synthetic peptides based on the KXFFX[1]R [SEQ ID NO:1] sequence. In addition to the linear peptides, some peptides were cyclized by adding cysteine residues at either ends. These experiments resulted in the identification of peptides which have distinct antagonistic specificities for the interaction of different hormone receptors with calreticulin.

In order to derive peptides which might be specific for one receptor over another one, we have undertaken the synthesis of a series of peptides listed in Table III.

These peptides were tested in gel mobility shift assays (described in Example 3) using equivalent concentrations of various receptors: retinoic acid receptors (RAR/RXR), vitamin D receptor (VDR), estrogen receptor (ER), androgen receptor (AR) and glucocorticoid receptor (GR), and their respective DNA response elements. These experiments identified specific peptides for use against individual receptors.

Experiments using the RAR/RXR, RXR/RXR or VDR/RXR receptors indicated that the KLGFFKR [SEQ ID NO:7] peptide was 10-fold more potent against the VDR/RXR heterodimer compared to RAR/RXR heterodimer, and was 4-fold more potent against the RXR/RXR heterodimer compared to the RAR/RXR receptor.

TABLE III

Proposed Peptides

| Proposed Peptides | [SEQ ID NO.:] | Variants | Exploring Protection | Exploring Hydrophobic Patch |
|---|---|---|---|---|
| RKFFGK d(KGFFKR) | [SEQ ID NO.: 32] | Reversed D-amino acid version | X | X |
| FGKKRK | [SEQ ID NO.: 33] | another scrambled peptide | X | |
| Ac-KGFFKR | [SEQ ID NO.: 34] | Acetylated peptide | X | |
| KGLFKR | [SEQ ID NO.: 35] | | | X |
| KGFLKR | [SEQ ID NO.: 36] | | | X |
| KGYFKR | [SEQ ID NO.: 37] | | | X |
| KGFYKR | [SEQ ID NO.: 38] | | | X |
| KGPFKR | [SEQ ID NO.: 39] | | | X |
| KGFPKR | [SEQ ID NO.: 40] | | | X |
| KFGFKR | [SEQ ID NO.: 41] | Inversion | | X |
| KGDFKR | [SEQ ID NO.: 42] | | | X |
| KGFKDR | [SEQ ID NO.: 43] | | | X |

Our data has also identified the amino acids within this sequence which are crucial for activity as shown in Table IV. Table IV shows that certain peptides exhibited selectivity for inhibiting calreticulin-receptor interaction in a receptor specific manner. This Table relates to the retinoic acid receptors (RAR/RXR) and the androgen receptor (AR). This data was obtained utilizing gel mobility shift assays as described previously (Example 3). The data was quantified using a Phosphormager (Molecular Dynamics).

TABLE IV

Relative Ability of Peptides to Reverse Calreticulin Inhibitions of Retinoic Acid Receptor (RAR/RXR) and Androgen Receptor (AR) Binding to Respective DNA Response Elements

| | | % Reversal | |
|---|---|---|---|
| | [SEQ ID NO.:] | RAR/RXR | AR |
| KLGFFKR | [SEQ ID NO.: 7] | 100% | 62% |
| KGFFKR | [SEQ ID NO: 5] | 100% | N.D. |
| KVFFKR | [SEQ ID NO: 3] | N.D. | 100% |
| KLRFGFK (scrambled sequence) | [SEQ ID NO.: 29] | 34% | n.d. |
| GLGFFKR | [SEQ ID NO.: 44] | 45% | 100% |
| KLDFFKR | [SEQ ID NO.: 45] | 73%* | 0%* |
| KLGRFKR | [SEQ ID NO.: 46] | 24% | 10% |
| KLGFRKR | [SEQ ID NO.: 47] | 20% | 6% |

TABLE IV-continued

Relative Ability of Peptides to Reverse Calreticulin Inhibitions of Retinoic Acid Receptor (RAR/RXR) and Androgen Receptor (AR) Binding to Respective DNA Response Elements

|   | [SEQ ID NO.:] | % Reversal | |
|---|---|---|---|
|   |   | RAR/RXR | AR |
| KLGFFGR | [SEQ ID NO.: 48] | 65% | 85%* |
| KLGFFKG | [SEQ ID NO.: 49] | 22%* | 63%* |

*significant selectivity of these peptides for one receptor over the other.

The most critical amino acids appear to be F, F, and R in the sequence KLGFFKR [SEQ ID NO:7]. These three amino acids are completely invariant in all steroid and nuclear hormone receptors as well as in integrins.

Thus using the RAR/RXR system in gel mobility shift assays, the two phenylalanines, as well as the terminal arginine, were found to be absolutely essential, since substitution of these resulted in the abrogation of the peptide activity (Table IV).

The peptides identified from these gel mobility shift assays are being used in cellular assays described below.

Retinoic acid-receptor specific peptides: These are tested in the P19 retinoic acid induced neuronal differentiation assay described in Example 5.

Vitamin D-receptor specific peptides: These are tested in the MC3T3-E1 osteoblastic cells which can be induced to differentiate into osteoblasts and form a calcified matrix (mineralize) with vitamin D. The ability to mineralize by monitoring $^{45}$Ca incorporation is determined after treatment with peptides.

Estrogen-receptor specific peptides: These are tested for ability to modulate estrogen-responsive breast cancer cell line proliferation. ER positive cells, e.g. MCF7 and T47-D are used.

Androgen-receptor specific peptides: These were tested in prostate carcinoma LnCAP cells which are androgen responsive and express the androgen-receptor. (Example 4)

Glucocorticoid-receptor specific assays: These are tested in dexamethasone treated peripheral blood lymphocytes.

Example 8
Regulation of Endogenous Level of Expression of Calreticulin

In murine P19 embryonal carcinoma cells, overexpression of calreticulin inhibits all-trans retinoic acid responsiveness, whereas downregulating calreticulin by antisense cDNA transfection results in an enhancement of retinoic acid response (see Example 5). In order to determine whether such modulation of calreticulin expression results in changes in the responsiveness to other steroid hormones and vitamins, the PRC-CMV based calreticulin vectors CAL-1 (sense cDNA) and CAL-2 (antisense cDNA) are used to stably transfect mouse osteoblastic cells (MC3T3 El), chicken osteoclast precursors, normal rat mammary epithelial cells (Darcy, 1991) and chemically transformed rat mammary adenocarcinoma cells (ATCC CRL1743), as well as estrogen and progesterone responsive human breast carcinoma cells (MCF-7 and T47-D).

Calreticulin expression levels in these cell types are determined at the outset by Western blot analysis. In addition to utilizing these stable expression vectors, we construct inducible calreticulin expression sense- and antisense-cDNA expression vectors driven by strong metal inducible promoters (Filmus et al., 1992). The inducible vectors allow us to turn calreticulin expression on or off at will. In the MC3T3 cells, 1,25,dihydroxyvitamin D3 has a proliferative effect on these cells at subconfluency, but when added to confluent, mineralizing cultures, it enhances the mineralization process. The transfected cells are analyzed for the level of calreticulin expression by Western blot analysis as described by us previously as well as by Northern blot analysis for mRNA levels. The effect of up or down regulation of calreticulin is determined in terms of the above mentioned responses to 1,25 dihydroxyvitamin D3. In addition, the effect on the expression of vitamin D responsive genes, such as c-fos and integrin b3 subunit (Xu et al., 1993) is determined by Northern blot and Western blot analysis. These cells are transfected with a reporter construct consisting of a vitamin D response element (VDRE) driving the luciferase gene. The luciferase activity in mock transfected versus calreticulin sense- and antisense-cDNA transfected cells (stable and inducible) is then be determined as described by us previously (see Example 6).

Similar experiments are carried out in chicken osteoclast precursors whose differentiation into mature osteoclasts is dependent upon vitamin D (Xu et al., 1993).

The effect of modulating calreticulin levels on the glandular differentiation of normal mammary epithelial cells is examined utilizing a cell culture model of differentiation (Darcy, 1991). Since steroid hormones such as estrogen and progesterone play crucial roles in this differentiation process, the effect of calreticulin on this system is determined. Similarly, the effect of modulating calreticulin expression in mammary carcinoma cell response to estrogen, Tamoxifen, progesterone and retinoic acid is determined. Since in cell lines such as MCF-7, estrogen induces proliferation, whereas Tamoxifen and all-trans retinoic acid inhibit proliferation (Pratt et al., 1993), modulating calreticulin levels results in the augmention of one response preferably over another one. Modulation of calreticulin levels is therapeutically significant in the control of breast cancer.

In addition to altering calreticulin levels by cDNA transfection, we determine whether calreticulin expression is modulated by growth factors, cytokines or steroid hormones and vitamins themselves. Although the promoter of the human calreticulin gene has been cloned and characterized (Michelak et al., 1992), it does not give any specific clues as to its regulation. In addition, it is conceivable that many compounds could regulate calreticulin levels at a post-transcriptional level. Factors which are known to influence the proliferation and differentiation of the above cell types (e.g. IGF-1 and vitamin D for osteoblasts; IL-6 for osteoclasts; EGF, FGF and TGF-b for mammary epithelial cells) are evaluated initially. We have already determined that 1,25,dihydroxyvitamin D3 upregulates calreticulin mRNA levels in the MC3T3 cells. Knowledge about the endogenous regulation of expression of calreticulin allow in vivo manipulation of nuclear hormone receptor-calreticulin interaction.

Example 9
Modulation of Hormone Receptor-Calreticulin Interaction by Peptides, Peptide Mimetics and Antibodies We have demonstrated that synthetic peptides based on the sequence KXFFX$^1$R [SEQ ID NO:1] can behave as competitive inhibitors of calreticulin-nuclear hormone receptor interaction (see Example 7). This was demonstrated by gel mobility shift assays. When incubated with the nuclear hormone receptor and calreticulin, the peptides can reverse the ability of calreticulin to inhibit receptor-DNA binding in vitro. Since a scrambled peptide was completely ineffective, this assay can distinguish peptide specificity. These data suggest that the interaction of calreticulin with the nuclear hormone receptors can be manipulated with such peptides.

We use the gel mobility shift assay and androgen receptor as well as the retinoic acid receptors (Shago et al., 1994) to determine which amino acids within the KXFFX$^1$R [SEQ ID NO:1] sequence are critical for the calreticulin-receptor interaction. This is done by synthesizing peptides with single amino acid substitutions and then testing them for their activity in gel mobility shift assays as described by us previously (see Example 7). Results from these experiments identify the critical amino acids in this sequence motif required for calretitulin-receptor interaction.

The nuclear hormone receptors can be subdivided into two categories, the steroid receptors, which include the androgen receptor, glucocorticoid receptor, mineralocorticoid receptor and estrogen receptor; and the thyroid hormone/retinoic acid receptor group which includes the retinoic acid receptors, thyroid hormone receptor and vitamin D receptor. Unlike the first category, this latter category of receptors bind to their DNA response elements as heterodimers with RXR. The above experiments therefore define the sequence motif for a receptor from each of these two categories i.e. androgen receptor and retinoic acid receptors (RAR/RXR; RXR/RXR). Subsequent experiments are then be carried out with other receptors such as estrogen receptor and vitamin D receptor.

The N-domain of calreticulin (Michalak et al., 1992) has been implicated in the interaction with the glucocorticoid receptor. We have prepared GST-fusion proteins in *E. coli* consisting of either full length human calreticulin, the N-domain, P-domain or the C-domain. Each of these recombinant proteins is tested in gel mobility shift assays (according to the teaching of Example 3) for their effectiveness in inhibiting receptor-DNA interaction. The receptors we use initially will be the androgen receptor and the retinoic acid receptors. P19 EC cells or Vero cells are also transiently transfected with expression vectors containing the N, P or C calreticulin domains, and their effect on hormone induced gene expression determined as described by us previously (see Example 5).

We have identified the calreticulin domain which interacts with the receptors. We will use proteolytic fragments of the recombinant proteins (generated by proteolytic cleavage and purification of peptides by HPLC) to further define the minimal peptide(s) necessary for mediating the interaction. If a sufficiently small peptide is found to be active, then synthetic peptides from within that sequence will be evaluated.

Example 10
Preparation and Testing of Delivery Systems for Peptide-antagonists of Calreticulin Nuclear Hormone Receptor Interactions After we identify peptides capable of inhibiting calreticulin-receptor interactions in vitro, we test the efficiency of these peptides on cells. To do this, the peptides are incorporated into cationic lipid vesicles (liposomes, such as lipofectin) and incubated with the cell types described in Example 9. To assess internalization of the peptides, some peptides are conjugated with fluorescein isothiocyanate (FITC). After incubation of the liposomes with the cells for different time periods, the cells are examined by immunofluorescence microscopy to assess intracellular accumulation. The biological effects of the peptides are determined by assessing hormonal sensitivity of the target cells, expression of primary response genes by Northern and Western blot analysis, and hormone-induced expression of luciferase reporter constructs containing various response elements, described in Example 6. The target cells and the hormone responsive parameters to be used are described in Example 7.

These experiments determine whether the peptides defined in Example 7 are functional at the cellular level in antagonizing hormone receptor-calreticulin interactions. Once we optimize the peptide delivery systems and achieve the predictable cellular responses, we test these peptide-liposomes in animal model systems such as bone formation in the mouse, and rat mammary gland differentiation. For the former, primary osteoblasts derived from mouse calvariae are injected into the gluteal muscle of recipient mice where these osteoblasts differentiate to form mineralized nodules. The effect of local or systemic administration of peptide-liposomes are then assessed in this model. Similarly the effect of the peptides on normal mammary gland development after injection of normal rat mammary epithelial cells into mammary fat pads (Darcy, 1991) are assessed. If the peptides are found to be effective in influencing these processes then their effect on animal models of osteoporosis, and growth and differentiation of human breast and prostate cancer xenografts in nude mice are determined.

The following examples relate to the manufacture and use of pharmaceuticals to treat particular diseases, including cancer, osteoporosis, and chronic inflammatory disease, using pharmaceuticals comprising a protein for use in modulating hormone responsiveness and a carrier.

Example 11
Method of Treating Prostate Cancer

Prostate cancer is the most frequently diagnosed invasive cancer and the second most common cause of cancer death in men in Western societies (Boring, 1993; Coffey, 1993). At present, prostate cancer patients are diagnosed with either locally invasive, or disseminated disease, and the currently available forms of treatment may prolong survival but are essentially only palliative (Scardino, 1992; Kozlowski, 1991; Santer, 1992).

Although primary endocrine ablation leads to an initial response in about 70% of patients with advanced disease, most patients relapse within three years and only about 20% survive for five years (Kozlowski, 1991). This rapid progression of prostate cancer following failure of primary hormone therapy is attributed to androgen-independent tumor growth.

In some androgen-insensitive rat as well as human prostate cancer cell lines, androgen independence is associated with a loss or decrease in androgen receptor (AR) mRNA and protein levels (Quarmby, 1990; Tilley, 1990). However some prostate carcinoma cell lines derived from metastases retain AR expression and androgen sensitivity (e.g. Ln CAP cell line). Furthermore there is evidence that some prostate cancer cells which continue to grow after initiation of anti-androgen therapy retain expression of AR (van der Kwast, 1991; Tilley, 1994). Similarly, AR expression is retained by androgen-independent mouse mammary tumors (Dabre, 1987).

These observations suggest that mechanisms other than the loss of AR expression are involved in the progression to an androgen-independent state. One explanation could be the presence of mutations in the AR gene in a subpopulation of tumor cells which results in aberrant regulation of growth by steroids. Indeed mutations in the AR gene have been detected in prostate cancer cells, although their significance in tumor progression is not yet clear. Another explanation might be alterations in the expression or function of components which regulate AR activity and AR dependent gene expression.

As described in previous Examples, calreticulin, can bind to nuclear hormone receptors by interacting with the KXFFX$^1$R [SEQ ID NO:1] sequence. The interaction results in a profound inhibition of nuclear hormone receptor DNA binding activity which can be reversed by soluble competing synthetic peptides with the generic sequence KXFFX$^1$R [SEQ ID NO:1].

The level of expression of calreticulin in prostate androgen-dependent and independent prostate cancer cells could have significant effects on androgen receptor activity. Furthermore, experimental manipulation of calreticulin levels in prostate cancer cells has resulted in the modulation of androgen-receptor activity.

For example, Table V shows that the expression of calreticulin increases with prostate cancer progression from benign to BPH (benign prostatic hyperplasia) to PIN (Prostatic Intraepithial Neoplasia) to cancer. This is an important finding liking calreticulin as a marker of prostate cancer progression and also as a target for therapy as described in this application.

TABLE V

| Patient | Normal | Atrophy | BPH | PIN | CA |
|---|---|---|---|---|---|
| Not treated | | | | | |
| 1 | 1+ | +/− | 2+ | 4+ | 3–4+ |
| 2 | 1–2+ | N/A | 3+ | 3–4+ | 3–4+ |
| 3 | 1–2+ | +/1 | 2+ | 4+ | 3–4+ |
| 4 | 2+ | 1+ | 2+ | 4+ | 2–3+ |
| 5 | 1–2+ | 1+ | 1–2+ | 3–4+ | 3–4+ |
| Treated | | | | | |
| 6 | 1+ | 1+ | N/A | 3+ | 2–3+ |
| 7 | 1–2+ | 1+ | 1–2+ | 3–4+ | 5–4+ |
| 8 | 1–2+ | 1+ | 1–2+ | 4+ | 3–4+ |
| 9 | +/− | 0 | N/A | 2+ | 1–2+ |
| 10 | 2+ | 2+ | N/A | 2+ | 2–4+ |

BPH: Benign prostatic hyperplasia
PIN: Prostatic intrapithelial neoplasia
CA: Carcinoma Parallel paraffin sections from prostate biopsies were stained with Hemotoscylin and Eosin or by in situ hybridization with a calreticulin-specific antisense DNA probe. Calreticulin mRNA expression was confined to the epithelial tissue and dramatically increased, within the same section, from benign regions to PIN and CA regions. The extent of signal was evaluated independently by three pathologists. Some sections were also stained with the sense probe as control which was negative.

In addition, the interaction of androgen receptors with calreticulin could be taken advantage of, theoretically, by utilizing calreticulin or calreticulin-derived peptides and peptide-mimetics for the inhibition of androgen receptor dependent prostate cancer cell growth. Such a therapeutic strategy might be particularly useful in recurrent, androgen-independent prostate cancers which retain expression of AR or mutant ARs and which may bind to DNA in the absence of androgen.

Calreticulin expression in the nuclear, cytoplasmic and microsomal fractions from human prostate carcinoma cell-lines PC-3, DU-145, LnCAP, as well as highly invasive variants of PC-3 cells (IPC31-3) (Dedhar, 1994) is determined by Western blot analysis utilizing two different polyclonal anti-calreticulin antibodies as described by us previously (Leung-Hagesteijn, 1994).

Expression at the level of mRNA is carried out using a 1.9 Kb calreticulin cDNA. Calreticulin expression in these cells is determined after treatment with androgens (for LnCAP cells which express AR, or for PC-3 cells transfected with AR, see below), retinoic acid, 1,25 dihydroxy vitamin D3, and growth factors such as epidermal growth factor and insulin-like growth factors.

A subset of a large (>125) tissue bank of frozen human prostate cancers (Sunnybrook Health Science Centre were treated with neo adjuvant androgen ablative therapy prior to resection. Each frozen block has been histologically characterized. The bank also contains hormone-resistant prostate cancer specimens and will accrue fresh bond marrow metastases from warm autopsies on patients dying of androgen resistant prostate cancer. These tissues are freely available for the aforementioned analyses. This permits determination of calreticulin expression in untreated, hormonally treated and hormone resistant disease.

Calreticulin expression in cryostat sections is determined by immunohistochemistry using the avidin-biotin complex method described by Hsu et al., 1981 as well as by in situ hybridization using antisense cDNA calreticulin probes as described by Naylor et al., 1990. Simultaneous determination of the androgen-receptor status in these tissues on serial sections are carried out using anti-AR antibodies (Tilley, 1994).

Overexpression, or inhibition of expression of calreticulin is carried out by stable transfection of sense (pRC-CMV-Cal1) or anti-sense (pRC-CMV-Cal2) (Dedhar, 1994) cDNA expression vectors into LnCAP or AR expressing PC-3 cells. AR expressing PC-3 cells are obtained from Dr. Paul Rennie, Vancouver, B.C. We have previously described the utility of these calreticulin expression vectors in manipulating hormone responsiveness (see Example 4). These cells are also transfecied with a tetracyclin inducible calreticulin expression vector. This expression plasmid, pUHD10-3-CAL, has been constructed and calreticulin sense or anti-sense mDNA expression is induced via a tetracyclin-operators. Calreticulin expression levels are determined by Western blot analysis as described above. The responsiveness of the transfected cells to androgens, in terms of cell growth, is then determined. Cell growth is determined by counting cell numbers as well as by $^3$H-thymidine incorporation. Calreticulin overexpression makes the cells non-responsive to androgens, whereas inhibition of calreticulin expression makes the cells more sensitive, as was the case for retinoic acid responsiveness in ECP19 cells (see Example 5). Stable overexpression of calreticulin does not alter intracellular calcium concentrations, and therefore the observed effects on hormone sensitivity are not due to effects on calcium levels.

The calreticulin transfected cells is compared with the parental or mock transfected cells for their abilities to form tumors in nude mice upon subcutaneous inoculation, or orthotopic inoculation into the prostate gland.

The domain of calreticulin which interacts with the KXFFX$^1$R [SEQ ID NO:1] sequence has been identified as the globular N-domain. This domain contains a putative ATP binding site and recombinant calreticulin can be phosphorylated in vitro on a serine residue within this domain (Leung-Hagesteijn, 1994). We have prepared GST-fusion proteins in E. Coli consisting of the full length human calreticulin, the N-domain, P-domain, or the acidic C-domain. Each of these recombinant peptides is tested in gel mobility shift assays for their effectiveness in the inhibition of androgen receptor-DNA interaction (see Example 10). These domains are tested for their effectiveness in inhibiting androgen mediated gene expressing by transiently expressing them in LnCAP or AR-expression PC-3 cells (described previously). Once we have identified the calreticulin domain which interacts with the androgen receptor (although this is likely to be the N-domain, based on previous work, see above), we derive proteolytic fragments from these proteins (by limited proteolytic cleavage using various proteases, and purification of peptides by high pressure liquid chromatography), and utilize these in gel mobility shift assays to further define the minimal peptide sequence required for interaction with the androgen receptor. If a sufficiently small peptide is found to be active, then synthetic peptides from within that sequence are evaluated further.

Peptides capable of inhibiting AR-DNA interactions in vitro are identified. In order to test the efficiency of these peptides in cells, the peptides are incorporated into cationic lipid vesicles (liposomes, such as lipofectin) and incubated with the cell types (see Example 11).

These experiments determine whether the peptides defined above are functional at the cellular level in antagonizing hormone receptor-DNA interactions. Once we have optimized the peptide delivery systems and achieve the predictable cellular responses, we test these peptide-liposomes in animal model systems described above.

These peptides, in conjunction with current protocols of androgen ablation, are useful in inhibiting androgen-receptor mediated prostate cancer cell growth. This strategy is useful not only in the early treatment of androgen-sensitive tumors, but also in more advanced androgen-resistant tumors which may express normal or mutated ARs which can induce cell growth in an androgen-independent manner. In such tumors, the maintenance of high levels of calreticulin expression, or of administration of calreticulin-based peptides (derived as described above), or peptide mimetics, provide a new mode of therapeutic intervention in the inhibition of prostate cancer cell growth and progression.

Example 12
Method of Treating Breast Cancer

We use a similar protocol as for prostate cancer (Example 11) but use proteins/mimetic selective for estrogen. Transfections are made into MCF-7, T47-D human breast cancer cells lines instead of LnCAP. For patient treatment, the peptides or their mimetics, or calreticulin or its mimetics are delivered in lipid vesicles prepared as described in Examples 10 and 11.

Example 13
Method of Treating Chronic Inflammatory Disease

The debilitating symptoms of chronic inflammatory diseases such as arthritis arise from inadvertent immune responses. Steroidal compounds are major immunosuppressive agents often used in the therapy of chronic inflammatory diseases. The response to such therapy may be dramatically augmented by the co-administration of calreticulin-hormone receptor antagonists based on the KXFFX$^1$R [SEQ ID NO:1] sequence. Such peptides, or their organic mimetics, may dramatically enhance the hormonal response by activating those receptors which may be bound by calreticulin. This may also result in the use of lower concentrations of the steroidal compounds, resulting in fewer side effects. The mode of delivery of such peptides or organic mimetics would be in lipid vesicles described in Examples 10 and 11.

Example 14
Method of Treating Osteoporosis

Osteoporosis results from an imbalance in the rate of bone resorption versus bone formation. Specifically, in post menopausal women, the decrease in systemic estrogen levels results in decreased bone formation in the face of continual osteoclast mediated bone resorption. Estrogen therapy, by using estrogen analogs which may specifically enhance osteoblast function and bone formation is under intensive study.

Given our findings that increased expression of calreticulin inhibits bone formation, the expression of calreticulin is likely increased in patients with osteoporosis. Therefore co-administration of KXFFX$^1$R [SEQ ID NO:1] based peptides or mimetics specific for the antagonism of calreticulin estrogen receptor interaction would be highly beneficial for this treatment. Such peptides or mimetics would dramatically increase the efficacy of estrogen analogs used in such therapy.

An alternative approach for the use of calreticulin based therapy would be inhibition of osteoclast differentiation. The differentiation of mature osteoclasts from osteoclast precursors is enhanced by Vitamin D3. The specific inhibition of the vitamin D receptor by calreticulin based mimetics would therefore result in the suppression of osteoclast mediated bone resorption. Combined therapy of increasing bone formation and down regulating bone resorption may be an effective treatment for osteoporosis.

The peptides or mimetics would once again be delivered by methods described in Examples 10 and 11.

Figure 5A:
Figure 5C:
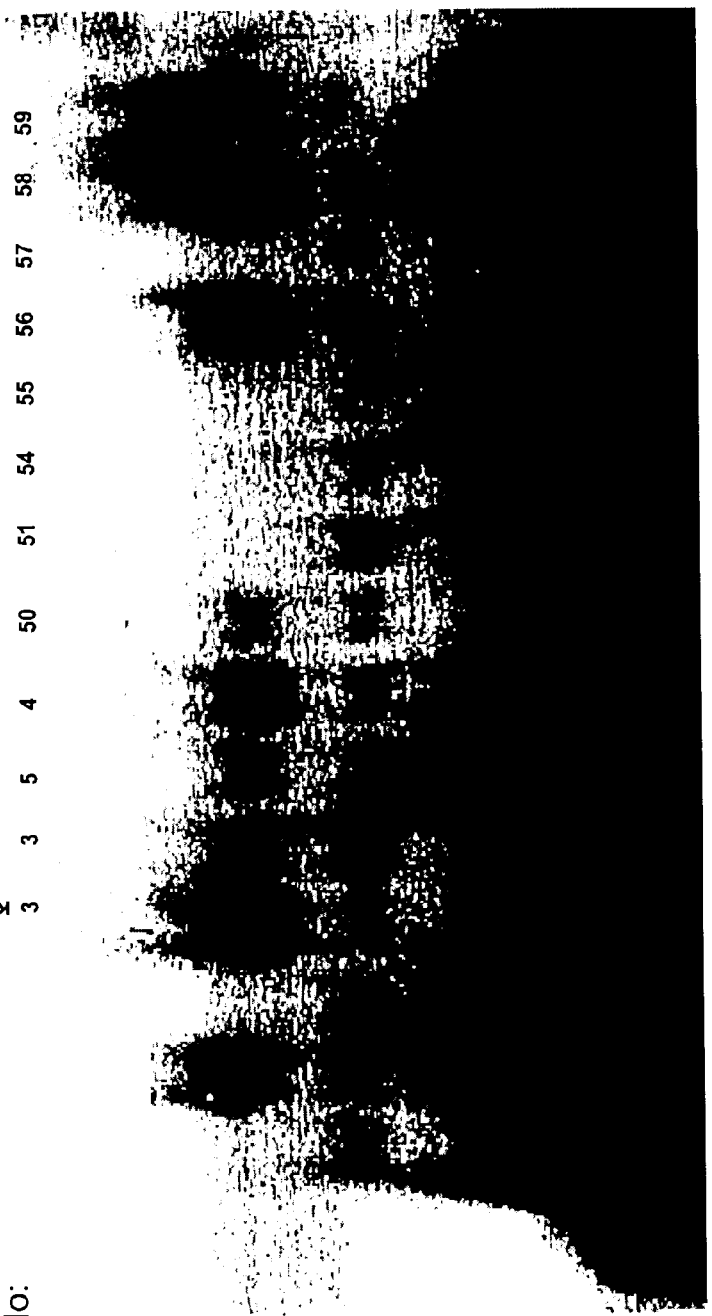

Example 15
Substitution of Phenylalanine with Basic Residues Increases the Effectiveness of Binding to Calreticulin Amino acids in the KXFFX$^1$R [SEQ ID NO: 1] sequence were modified. Sequences of the modified peptides are shown in Table VI. Androgen receptor and calreticulin were incubated in the presence of the modified peptides and allowed to interact with an oligonucleotide containing the androgen response element (the method of this assay is described in Example 3). The interaction was analyzed by gel mobility shaft assay (FIGS. 5A–5C).

It was shown that changes in amino acid sequence affect binding responsiveness. Substitution of phenylalanine with highly basic residues (such as arginine) increased the effectiveness of binding to calreticulin. See the results obtained with peptides 414, 415, 420, 420 and 421 in Table VI. Replacing phenylalanine and arginine with neutral amino acids decreased the ability of peptides to bind calreticulin. This is shown by the results obtained with peptides 416, 417, 427, 429 and 430 in Table IV.

It was shown that changes in amino acid sequence affect binding responsiveness. Substitution of phenylalanine with highly basic residues (such as arginine) increased the effectiveness of binding to calreticulin. See the results obtained with peptides 414, 415, 420 and 421 in Table VIII. Replacing phenylalanine and arginine with neutral amino acids decreased the ability of peptides to bind calreticulin. This is shown by the results obtained with peptides 416, 417, 427, 429 and 430 in Table V.

Table VIII

Substitution of Phenylalanine with Highly Basic Amino Acid Residues and Neutral Amino Acid Residues

| Number | Sequence | [SEQ ID NO:] | Competes with Androgen Receptor for Calreticulin binding (band shift) |
|---|---|---|---|
| 285 | KVFFKR | [SEQ ID NO: 3] | + |
| 409 | KGFFKR | [SEQ ID NO: 5] | + |
| 410 | KGFFRR (5 µG) | [SEQ ID NO: 2] | −/+ |
| 411 | KAFFKR | [SEQ ID NO: 4] | + |
| 412 | GGFFKR | [SEQ ID NO: 50] | +/− |
| 413 | KDFFKR | [SEQ ID NO: 51] | − |

Table VIII-continued

Substitution of Phenylalanine with Highly Basic Amino Acid Residues and Neutral Amino Acid Residues

| Number | Sequence | [SEQ ID NO:] | Competes with Androgen Receptor for Calreticulin binding (band shift) |
|---|---|---|---|
| 414 | KGRFKR | [SEQ ID NO: 52] | ++ |
| 415 | KGFRKR | [SEQ ID NO: 53] | ++ |
| 416 | KGFFGR | [SEQ ID NO: 54] | − |
| 417 | KGFFKG | [SEQ ID NO: 55] | − |
| 418 | GGFFRR | [SEQ ID NO: 56] | + |
| 419 | KDFFRR | [SEQ ID NO: 57] | − |
| 420 | KGRFRR | [SEQ ID NO: 58] | ++ |
| 421 | KGFRRR | [SEQ ID NO: 59] | ++ |
| 422 | KGFFRG | [SEQ ID NO: 60] | +/− |
| 423 | KGFFKK | [SEQ ID NO: 61] | − |
| 424 | KVFFKR (all D) | | + |
| 425 | KGFFKR (all D) (5 µG) | | + |
| 426 | AVFFKR | [SEQ ID NO: 62] | +/− |
| 427 | KVAFKR | [SEQ ID NO: 63] | − |
| 428 | KVFFAR | [SEQ ID NO: 64] | +/− |
| 429 | KVFAKR | [SEQ ID NO: 65] | − |
| 430 | KVFFKA | [SEQ ID NO: 66] | − |
| 431 | KV$_{(N\text{-}acetylated)}$AFKR | [SEQ ID NO: 63] | ++ |

Further examples are found in Canadian Application No. 2,140,814, filed Jan. 23, 1995 and entitled, "Use of Calreticulin in Modulating Hormone Responsiveness and New Pharmaceuticals for Treating Cancer, Osteoporosis and Chronic Inflammatory Disease", which is incorporated herein by reference in its entirety.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. For example, due to codon redundancy, changes can be made in the underlying DNA sequence without affecting the protein sequence. Moreover, due to biological functional equivalency considerations, changes can be made in protein structure without affecting the biological action in kind or amount. All such modifications are intended to be included within the scope of the appended claims.

REFERENCES

The documents listed below are incorporated herein by reference to the extent that they supplement, explain, provide a background for, or teach methodology, techniques and/or compositions employed herein.

Alexander J. E., Hunt D. F., Lee M. K., et al. *Proc. Natl. Acad. Sci. USA* 88:4685–4689 (1991).
Baksh S. and Michalak M. *J. Biol. Chem.* 266:21458–21465 (1991).
Boring C. C., et al. *CA Cancer J. Clin.* 43:7 (1993).
Burns K., Duggan B., Atkinson E. A., Famulski K. S., Nemer M., Bleakley R. C., and Michalak M. Modulation of gene expression by calreticulin binding to the glucocorticoid receptor. *Nature*, 367:476–480 (1994).
Carson-Jurica M., Schrader W. T. and O'Malley B. W. *Endocrine Rev.* 11:201–220 (1990).
Coffey D. S. *Cancer* 71(suppl 3):880 (1993).
Current Protocols in Molecular Biology 9:1.
Dabre P. D., et al. *Cell* 51:521 (1987).
Darcy K. M. *Exp. Cell Res.*, 196:49–65 (1991).
de The H., Marchio A., Tiollais P. and Dejean A. *Nature* 343:1771–1780 (1990).
Dedhar S. Novel functions for calreticulin: interaction with integrins and modulation of gene expression? *Trends Biochem. Sciences* 19:269–271 (1994).
Dedhar S., Rennie P. S., Shago M., Leung-Hagesteijn C., Yang H., Filmus J., Hawley R.G., Bruchovsky N., Cheng H., Matusik R. J. and Giguere V. Inhibition of Nuclear Hormone Receptor Activity by calreticulin. *Nature*, 367:480–483 (1994).
Dedhar S., et al. *Clin. Exp. Metastasis* 11:391 (1993).
Dedhar S., Robertson K. and Gray V. *J. Biol. Chem.*, 266:21846–21852 (1991).
Dedhar S. Signal transduction via the $b_1$ integrins is a required intermediate in interleukin-1b induction of alkaline phosphatase activity in human osteosarcoma cells. *Exp. Cell Res.*, 183:207–214 (1989).
Filmus J., Remani, J. and Klein M. H. Synergistic induction of promoters containing metal- and glucocorticoid-responsive elements. *Nucleic Acids Res.*, 20:2755–2760 (1992).
Fliegel L., Burns K., MacLennan D. H., Reitheimer, R. A. F. and Michalak M. J. *Biol. Chem.* 264:21522–21528 (1989a).
Fliegel L., Burns K., Opas M. and Michalak M. The high-affinity calcium binding protein of sarcoplasmic reticulum. Tissue distribution, and homology with calregulin. *Biochem. Biophys. Acta.* 982:1–8 (1989).
Fuller P. J. *FASEB J.*, 5:3092–3099 (1991).
Giguere V., Lyn S., Yin P. et al. *Proc. Nati. Acad. Sci. USA* 87:6233–6237 (1990).
Hard T., Kellenbach E., Bochens R., et al. *Science* 249:157–160 (1990).
Hsu S. M., et al. *J. Histochem. Cytochem.* 29:577 (1981).
Kozlowski J. M., et al. *The Urologic Clinics of North America* (W. B. Saunders Co., Philadelphia), p. 15–24 (1991).
Lebeau M.-C., Massol N., Herrick J., et al. *J. Biol. Chem.* 267:4281–4284 (1992).
Lee M. K., Tuttle J. B. and Rebhun L. I., et al. *Cell Motil. Cytoskel.* 17:118–132 (1990).
Leung-Hagesteijn C., Milankov K., Michalak M., Wilkins J. and Dedhar S. Cell attachment to extracellular matrix substrates is inhibited upon downregulation of expression of calreticulin, an intracellular integrin alpha-subunit-binding protein. *J. Cell Sci.* 107:589–600 (1994).
Luisi B. F., Xu W. X., Otwinowski Z., Freedman L. P., Yamamoto K. R. and Sigler P. B. Crystallographic analysis of the interaction of the glucocorticoid receptor with DNA. *Nature* 352:497–505 (1991).
Marzluff W. F. and Huang R. C. C. in *Transcription and Translation: A practical approach.* Oxford University Press, Oxford p. 89–129 (1985).
McBurney, M. W. and Rogers B. J. *Dev. Biol.* 89:503 (1982).
McCauliffe D. P., Yang Y.-S., Wilson J., Sontheimer R. D. and Capra J. D. The 5'-flanking region of the human calreticulin gene shares homology with the human GRP78, GRP94, and protein disulfide isomerase promoters. *J. Biol. Chem.* 267:2557–2562 (1992).
McCauliffe D. P., Lux F. A., Liu T. S., et al. *J. Clin. Invest.* 85:1379–1391 (1990).
McCauliffe D. P., Zappi E., Liu T. S., Michalak M., Sontheimer R. D. and Capra J. D. *J. Clin. Invest.* 86:332–335 (1990).

Michalak M., Milner R. E., Burns K. and Opas M. Calreticulin. *Biochem. J.* 285:681 (1992).

Morgan and Gainor, *Ann. Rep. Med. Chem.,* 24:243–252 (1989).

Morrison N. A. *Nature,* 367:284–287 (1994).

Naylor S. M., et al. *Eur. J. Biochem.* 26:1027 (1990).

O'Malley B.W. The steroid hormone receptor superfamily: more excitement for the future. *Mol. Endocrin.,* 4:363–369 (1990).

Opas M., Dziak E., Fliegel L. and Michalak M. Regulation of expression and intracellular distribution of calreticulin, a major calcium binding protein of non-muscle cells. *J. Cell. Physiol.* 149:160–171 (1991).

Ostwald T. J. and MacLennan D. H. Isolation of a high affinity calcium-binding protein from sarcoplasmic reticulin. *J. Biol. Chem.* 249:974–979 (1974).

Pratt S. E. and Pollak M. *Cancer Res.* 53:5193–5198 (1993).

Quarmby V. E., et al. *Cancer Res.* 50:735 (1990).

Remington's Pharmaceutical Sciences, Mack Publishing Co., Easton, Pa., USA, 18th Edition (1990).

Rennie P. S., Bruchovsky N., Leco K. J., et al. *Mol. Endocrin.* 7:23–36 (1993).

Rojiani M., Finlay B. B., Gray V. and Dedhar S. *Biochemistry* 30:9859–9866 (1991).

Santer R. J., *J. Clin. Endocrinol. Metab.* 75:685 (1992).

Scardino P. T., et al. *Human Pathol.* 23:211 (1992).

Schwabe J. W. R., Chapman L., Finch J. T. and Rhodes D. The crystal structure of the estrogen receptor DNA-binding domain bound to DNA: how receptors discriminate between their response elements. *Cell* 75: 567–578 (1993).

Seed B. and Sheen J. Y. *Gene* 67:271 (1988).

Shago M., Flock G., Leung-Hagesteijn C., Giguere V. and Dedhar S. Modulation of the retinoic acid and retinoid X receptor signalling pathways in P19 embryonal carcinoma cells by the calcium binding protein calreticulin. *Cell Growth and Differentiation,* Submitted 1994.

Sucov H., Murakami K. K. and Evans R. M. *Proc. Natl. Acad. Sci. USA* 87:5392–5396 (1990).

Tai P.-K. K., Albers M. W., Chang H., Saber L. E. and Schreiber S. L. *Science* 256:1315–1318 (1992).

Tilley W. D., et al. *Cancer Res.* 54:4096 (1994).

Tilley W. D., et al. *Cancer Res.* 50:5382 (1990).

Tini M., Otulakowski G., Breitman M. L. et al. *Genes & Dev.* 7:295–307 (1993).

van der Kwast T. H., et al. *Int. J. Cancer* 48:189 (1991).

Xu C., Ross F.P., Zhang L., MacDonald P. N., Chappel J. and Teitelbaum S. L. Cloning of the promoter for the avian integrin b3 subunit gene and its regulation by 1,25 dihydroxyvitamin D3. *J. Biol. Chem.,* 268: 27371–27380 (1993).

I claim:

1. An isolated and purified peptide of 6 to 100 amino acids comprising the amino acid sequence KXFFKR wherein X is G, A or V (SEQ ID NO:68), with the proviso that the prptide is not KGFFKR, KAFFKR, KVFFKR or Ac-SCEGCKAFFKRS-[$^3$H]I-OG (SEQ ID NO:70), and wherein the peptide binds calreticulin.

2. An isolated peptide of 6 to 100 amino acids comprising the amino acid sequence KXFFRR (SEQ ID NO:69), wherein X is G, A or V, with the proviso that the peptide is not KGFFRR, KAFFRR, KVFFRR and wherein the peptide binds calreticulin.

3. An isolated peptide of 7 to 100 amino acids comprising an amino acid sequence selected from the group consisting of KGFFRR (aa 6–11 of SEQ ID NO.: 18), KVFFKR (SEQ ID NO.:3), KAFFKR (aa 6–11 of SEQ ID NO.:24), KGFFKR (aa 6–11 of SEQ ID NO.:25), TGFFKR (aa 6–11 of SEQ ID NO.:26), RKFFGK (SEQ ID NO.:32), d(CKGFFKR), FGKKRK (SEQ ID NO.:33), Ac-KGFFKR (SEQ ID NO.:34), KGLFKR (SEQ ID NO.:35), KGFLKR (SEQ ID NO.:36), KGYFKR (SEQ ID NO.:37), KGFYKR (SEQ ID NO.:38), KGPFKR (SEQ ID NO.:39), KGFPKR (SEQ ID NO.:40), KFGFKR (SEQ ID NO.:41), KGDFKR (SEQ ID NO.:42) and KGFKDR (SEQ ID NO.:43), with the proviso that the peptide is not Ac-SCEGCKAFFKRS-[$^3$H]I-OG(SEQ ID NO:70) wherein the peptide binds calreticulin.

4. An isolated peptide of 7 to 100 amino acids comprising an amino acid sequence selected from the group consisting of GLGFFKR (SEQ ID NO.:44), KLDFFKR (SEQ ID NO.:45), and KLGFFGR (SEQ ID NO.:48), wherein the peptide binds calreticulin.

* * * * *

```
                          SEQUENCE LISTING (1) GENERAL INFORMATION:

(iii) NUMBER OF SEQUENCES: 70

(2) INFORMATION FOR SEQ ID NO: 1:

(i) SEQUENCE CHARACTERISTICS:
          (A) LENGTH: 6 amino acids
          (B) TYPE: amino acid
          (C) STRANDEDNESS: single
          (D) TOPOLOGY: linear (ii) MOLECULE TYPE: peptide (ix) FEATURE:
          (A) NAME/KEY: Peptide
          (B) LOCATION: 2
          (D) OTHER INFORMATION: /note= "Amino acid 2 wherein Xaa is
              either Gly, Ala or Val."

(ix) FEATURE:
          (A) NAME/KEY: Peptide
          (B) LOCATION: 5
          (D) OTHER INFORMATION: /note= "Amino acid 5 wherein Xaa is
              either Lys or Arg."

(xi) SEQUENCE DESCRIPTION: SEQ ID NO: 1:

Lys Xaa Phe Phe Xaa Arg
1               5

(2) INFORMATION FOR SEQ ID NO: 2:

(i) SEQUENCE CHARACTERISTICS:
          (A) LENGTH: 6 amino acids
          (B) TYPE: amino acid
          (C) STRANDEDNESS: single
          (D) TOPOLOGY: linear (ii) MOLECULE TYPE: peptide
```

(xi) SEQUENCE DESCRIPTION: SEQ ID NO: 2:

Lys Gly Phe Phe Arg Arg
1               5

(2) INFORMATION FOR SEQ ID NO: 3:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 3:

Lys Val Phe Phe Lys Arg
1               5

(2) INFORMATION FOR SEQ ID NO: 4:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 4:

Lys Ala Phe Phe Lys Arg
1               5

(2) INFORMATION FOR SEQ ID NO: 5:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 5:

Lys Gly Phe Phe Lys Arg
1               5

(2) INFORMATION FOR SEQ ID NO: 6:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 6:

Thr Gly Phe Phe Lys Arg
1               5

(2) INFORMATION FOR SEQ ID NO: 7:

(i) SEQUENCE CHARACTERISTICS:
        (A) LENGTH: 7 amino acids
        (B) TYPE: amino acid
        (C) STRANDEDNESS: single
        (D) TOPOLOGY: linear

```
    (ii) MOLECULE TYPE: peptide (xi) SEQUENCE DESCRIPTION: SEQ ID NO: 7:

Lys Leu Gly Phe Phe Lys Arg
1               5

(2) INFORMATION FOR SEQ ID NO: 8:

(i) SEQUENCE CHARACTERISTICS:
        (A) LENGTH: 71 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 8:

Lys Pro Cys Phe Val Cys Gln Asp Lys Ser Ser Cys Tyr His Tyr Cys
1               5                   10                  15

Val Ser Ala Cys Glu Gly Cys Lys Gly Phe Phe Arg Arg Ser Ile Gln
            20                  25                  30

Lys Asn Met Val Tyr Thr Cys His Arg Asp Lys Asn Cys Gln Asp Lys
        35                  40                  45

Ser Ser Cys Tyr His Tyr Cys Val Ser Ala Cys Arg Leu Gln Lys Cys
        50                  55                  60

Phe Glu Val Gly Met Ser Lys
65                  70

(2) INFORMATION FOR SEQ ID NO: 9:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 9:

Xaa Gly Phe Phe Lys Arg
1               5

(2) INFORMATION FOR SEQ ID NO: 10:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 10:

Lys Xaa Gly Phe Phe Xaa Arg
1               5

(2) INFORMATION FOR SEQ ID NO: 11:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 11:
```

```
Lys Ile Gly Phe Phe Lys Arg
1               5
```

(2) INFORMATION FOR SEQ ID NO: 12:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 12:

```
Lys Cys Gly Phe Phe Lys Arg
1               5
```

(2) INFORMATION FOR SEQ ID NO: 13:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 13:

```
Lys Ala Gly Phe Phe Lys Arg
1               5
```

(2) INFORMATION FOR SEQ ID NO: 14:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 14:

```
Lys Cys Gly Phe Phe Asp Arg
1               5
```

(2) INFORMATION FOR SEQ ID NO: 15:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 15:

```
Arg Met Gly Phe Phe Lys Arg
1               5
```

(2) INFORMATION FOR SEQ ID NO: 16:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 16:

Lys Val Gly Phe Phe Lys Arg
1               5

(2) INFORMATION FOR SEQ ID NO: 17:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 17:

Lys Cys Gly Phe Phe Asn Arg
1               5

(2) INFORMATION FOR SEQ ID NO: 18:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 18:

Ala Cys Glu Gly Cys Lys Gly Phe Phe Arg Arg Ser Ile Gln Lys
1               5                   10                  15

(2) INFORMATION FOR SEQ ID NO: 19:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 19:

Thr Cys Glu Gly Cys Lys Gly Phe Phe Arg Arg Thr Ile Gln Lys
1               5                   10                  15

(2) INFORMATION FOR SEQ ID NO: 20:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 20:

Thr Cys Glu Gly Cys Lys Gly Phe Phe Arg Arg Ser Met Lys Arg
1               5                   10                  15

(2) INFORMATION FOR SEQ ID NO: 21:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 21:

Thr Cys Gly Ser Cys Lys Val Phe Phe Lys Arg Ala Val Glu Gly
1               5                   10                  15

(2) INFORMATION FOR SEQ ID NO: 22:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 22:

Thr Cys Gly Ser Cys Lys Val Phe Phe Lys Arg Ala Ala Ala Gly
1               5                   10                  15

(2) INFORMATION FOR SEQ ID NO: 23:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 23:

Thr Cys Gly Ser Cys Lys Val Phe Phe Lys Arg Ala Met Glu Gly
1               5                   10                  15

(2) INFORMATION FOR SEQ ID NO: 24:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 24:

Ser Cys Glu Gly Cys Lys Ala Phe Phe Lys Arg Ser Ile Gln Gly
1               5                   10                  15

(2) INFORMATION FOR SEQ ID NO: 25:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 25:

Ser Cys Glu Gly Cys Lys Gly Phe Phe Lys Arg Thr Val Arg Lys
1               5                   10                  15

(2) INFORMATION FOR SEQ ID NO: 26:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 26:

Thr Cys Glu Gly Cys Thr Gly Phe Phe Lys Arg Ser Ile Arg Lys
1               5                   10                  15

(2) INFORMATION FOR SEQ ID NO: 27:

(i) SEQUENCE CHARACTERISTICS:
            (A) LENGTH: 15 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 27:

Thr Cys Glu Gly Cys Lys Gly Phe Phe Lys Arg Thr Val Gln Lys
1               5                   10                  15

(2) INFORMATION FOR SEQ ID NO: 28:

(i) SEQUENCE CHARACTERISTICS:
            (A) LENGTH: 26 base pairs
            (B) TYPE: nucleic acid
            (C) STRANDEDNESS: double
            (D) TOPOLOGY: linear (ii) MOLECULE TYPE: DNA (genomic)

(xi) SEQUENCE DESCRIPTION: SEQ ID NO: 28:

GTAAAGTACT CCAAGAACCT ATTTGT                                        26

(2) INFORMATION FOR SEQ ID NO: 29:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 29:

Lys Leu Arg Phe Gly Phe Lys
1               5

(2) INFORMATION FOR SEQ ID NO: 30:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 30:

Lys Xaa Gly Phe Phe Lys Arg
1               5

(2) INFORMATION FOR SEQ ID NO: 31:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 31:

Lys Leu Xaa Phe Phe Lys Arg
1               5

(2) INFORMATION FOR SEQ ID NO: 32:

(i) SEQUENCE CHARACTERISTICS:
            (A) LENGTH: 6 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 32:

Arg Lys Phe Phe Gly Lys
1               5

(2) INFORMATION FOR SEQ ID NO: 33:

(i) SEQUENCE CHARACTERISTICS:
            (A) LENGTH: 6 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 33:

Phe Gly Lys Lys Arg Lys
1               5

(2) INFORMATION FOR SEQ ID NO: 34:

(i) SEQUENCE CHARACTERISTICS:
            (A) LENGTH: 6 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Peptide
            (B) LOCATION: 1
            (D) OTHER INFORMATION: /note= "Amino acid 1 wherein Lys is
                acetylated."

(xi) SEQUENCE DESCRIPTION: SEQ ID NO: 34:

Lys Gly Phe Phe Lys Arg
1               5

(2) INFORMATION FOR SEQ ID NO: 35:

(i) SEQUENCE CHARACTERISTICS:
            (A) LENGTH: 6 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 35:

Lys Gly Leu Phe Lys Arg
1               5

(2) INFORMATION FOR SEQ ID NO: 36:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 36:

Lys Gly Phe Leu Lys Arg
1               5

(2) INFORMATION FOR SEQ ID NO: 37:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 37:

Lys Gly Tyr Phe Lys Arg
1               5

(2) INFORMATION FOR SEQ ID NO: 38:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 38:

Lys Gly Phe Tyr Lys Arg
1               5

(2) INFORMATION FOR SEQ ID NO: 39:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 39:

Lys Gly Pro Phe Lys Arg
1               5

(2) INFORMATION FOR SEQ ID NO: 40:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 40:

Lys Gly Phe Pro Lys Arg
1               5

(2) INFORMATION FOR SEQ ID NO: 41:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 41:

Lys Phe Gly Phe Lys Arg
1               5

(2) INFORMATION FOR SEQ ID NO: 42:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 42:

Lys Gly Asp Phe Lys Arg
1               5

(2) INFORMATION FOR SEQ ID NO: 43:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 43:

Lys Gly Phe Lys Asp Arg
1               5

(2) INFORMATION FOR SEQ ID NO: 44:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 44:

Gly Leu Gly Phe Phe Lys Arg
1               5

(2) INFORMATION FOR SEQ ID NO: 45:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 45:

Lys Leu Asp Phe Phe Lys Arg
1               5

(2) INFORMATION FOR SEQ ID NO: 46:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 46:

Lys Leu Gly Arg Phe Lys Arg
1               5

(2) INFORMATION FOR SEQ ID NO: 47:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 47:

Lys Leu Gly Phe Arg Lys Arg
1               5

(2) INFORMATION FOR SEQ ID NO: 48:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 48:

Lys Leu Gly Phe Phe Gly Arg
1               5

(2) INFORMATION FOR SEQ ID NO: 49:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 49:

Lys Leu Gly Phe Phe Lys Gly
1               5

(2) INFORMATION FOR SEQ ID NO: 50:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 50:

Gly Gly Phe Phe Lys Arg
1               5

(2) INFORMATION FOR SEQ ID NO: 51:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 51:

Lys Asp Phe Phe Lys Arg
1               5

(2) INFORMATION FOR SEQ ID NO: 52:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 52:

Lys Gly Arg Phe Lys Arg
1               5

(2) INFORMATION FOR SEQ ID NO: 53:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 53:

Lys Gly Phe Arg Lys Arg
1               5

(2) INFORMATION FOR SEQ ID NO: 54:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 54:

Lys Gly Phe Phe Gly Arg
1               5

(2) INFORMATION FOR SEQ ID NO: 55:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 55:

Lys Gly Phe Phe Lys Gly

```
1               5

(2) INFORMATION FOR SEQ ID NO: 56:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 56:

Gly Gly Phe Phe Arg Arg
1               5

(2) INFORMATION FOR SEQ ID NO: 57:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 57:

Lys Asp Phe Phe Arg Arg
1               5

(2) INFORMATION FOR SEQ ID NO: 58:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 58:

Lys Gly Arg Phe Arg Arg
1               5

(2) INFORMATION FOR SEQ ID NO: 59:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 59:

Lys Gly Phe Arg Arg Arg
1               5

(2) INFORMATION FOR SEQ ID NO: 60:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 60:
```

```
Lys Gly Phe Phe Arg Gly
1               5

(2) INFORMATION FOR SEQ ID NO: 61:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 61:

Lys Gly Phe Phe Lys Lys
1               5

(2) INFORMATION FOR SEQ ID NO: 62:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 62:

Ala Val Phe Phe Lys Arg
1               5

(2) INFORMATION FOR SEQ ID NO: 63:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 3
        (D) OTHER INFORMATION: /note= "Amino acid 3 wherein Ala may
            be acetylated."

(xi) SEQUENCE DESCRIPTION: SEQ ID NO: 63:

Lys Val Ala Phe Lys Arg
1               5

(2) INFORMATION FOR SEQ ID NO: 64:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 64:

Lys Val Phe Phe Ala Arg
1               5

(2) INFORMATION FOR SEQ ID NO: 65:

(i) SEQUENCE CHARACTERISTICS:
        (A) LENGTH: 6 amino acids
        (B) TYPE: amino acid
```

(C) STRANDEDNESS: single
            (D) TOPOLOGY: linear (ii) MOLECULE TYPE: peptide (xi) SEQUENCE DESCRIPTION: SEQ ID NO: 65:

Lys Val Phe Ala Lys Arg
1               5

(2) INFORMATION FOR SEQ ID NO: 66:

(i) SEQUENCE CHARACTERISTICS:
            (A) LENGTH: 6 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 66:

Lys Val Phe Phe Lys Ala
1               5

(2) INFORMATION FOR SEQ ID NO: 67:

(i) SEQUENCE CHARACTERISTICS:
            (A) LENGTH: 6 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Peptide
            (B) LOCATION: 3, 4, 5
            (D) OTHER INFORMATION: /note= "Xaa is a basic amino acid"

(xi) SEQUENCE DESCRIPTION: SEQ ID NO: 67:

Lys Gly Xaa Xaa Xaa Arg
1               5

(2) INFORMATION FOR SEQ ID NO: 68:

(i) SEQUENCE CHARACTERISTICS:
            (A) LENGTH: 6 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Peptide
            (B) LOCATION: 2
            (D) OTHER INFORMATION: /note= "Amino acid 2 wherein Xaa is
                either Gly, Ala or Val."

(xi) SEQUENCE DESCRIPTION: SEQ ID NO: 68:

Lys Xaa Phe Phe Lys Arg
1               5

(2) INFORMATION FOR SEQ ID NO: 69:

(i) SEQUENCE CHARACTERISTICS:
            (A) LENGTH: 6 amino acids
            (B) TYPE: amino acid
            (C) STRANDEDNESS: single
            (D) TOPOLOGY: linear (ii) MOLECULE TYPE: peptide

```
    (ix) FEATURE:
         (A) NAME/KEY: Peptide
         (B) LOCATION: 2
         (D) OTHER INFORMATION: /note= "Amino acid 2 wherein Xaa is
             either Gly, Ala or Val."

(xi) SEQUENCE DESCRIPTION: SEQ ID NO: 69:

Lys Xaa Phe Phe Arg Arg
1               5

(2) INFORMATION FOR SEQ ID NO: 70:

(i) SEQUENCE CHARACTERISTICS:
         (A) LENGTH: 15 amino acids
         (B) TYPE: amino acid
         (C) STRANDEDNESS: single
         (D) TOPOLOGY: linear (ii) MOLECULE TYPE: peptide (ix) FEATURE:
         (A) NAME/KEY: Peptide
         (B) LOCATION: 1
         (D) OTHER INFORMATION: /note= "Amino acid 1 is acetylated."

(xi) SEQUENCE DESCRIPTION: SEQ ID NO: 70:

Ser Cys Glu Gly Cys Lys Ala Phe Phe Lys Arg Ser Ile Gln Gly
1               5                   10                  15
```